(12) United States Patent
Hunter

(10) Patent No.: US 12,138,029 B2
(45) Date of Patent: Nov. 12, 2024

(54) DEVICES, SYSTEMS AND METHODS FOR USING AND MONITORING SPINAL IMPLANTS

(71) Applicant: CANARY MEDICAL SWITZERLAND AG, Baar (CH)

(72) Inventor: William L. Hunter, Vancouver (CA)

(73) Assignee: Canary Medical Switzerland AG, Baar (CH)

( * ) Notice: Subject to any disclaimer, the term of this patent is extended or adjusted under 35 U.S.C. 154(b) by 0 days.

(21) Appl. No.: 17/981,269

(22) Filed: Nov. 4, 2022

(65) Prior Publication Data
US 2023/0233096 A1    Jul. 27, 2023

Related U.S. Application Data

(63) Continuation of application No. 16/447,766, filed on Jun. 20, 2019, now abandoned, which is a
(Continued)

(51) Int. Cl.
*A61F 2/44* (2006.01)
*A61B 5/00* (2006.01)
(Continued)

(52) U.S. Cl.
CPC ............ *A61B 5/036* (2013.01); *A61B 5/4566* (2013.01); *A61B 5/4851* (2013.01); *A61B 17/00* (2013.01); *A61B 17/70* (2013.01); *A61B 17/7032* (2013.01); *A61B 17/7035* (2013.01); *A61B 17/7037* (2013.01); *A61B 17/7049* (2013.01); *A61B 17/7059* (2013.01); *A61B 17/7074* (2013.01); *A61B 17/80* (2013.01); *A61B 90/06* (2016.02); *A61F 2/44* (2013.01); *A61F 2/442* (2013.01); *A61F 2/4455* (2013.01); *A61F 2/4611* (2013.01); *A61B 5/0031* (2013.01); *A61B 5/6853* (2013.01); *A61B 5/686* (2013.01); *A61B 2017/00221* (2013.01); *A61B 2090/064* (2016.02); *A61B 2090/065* (2016.02); *A61B 2505/05* (2013.01); *A61B 2560/0219* (2013.01);
(Continued)

(58) Field of Classification Search
CPC ........................ A61F 2/4455; A61F 2002/448
See application file for complete search history.

(56) References Cited

U.S. PATENT DOCUMENTS

| | | |
|---|---|---|
| 4,308,862 A | 1/1982 | Kalmar |
| 4,817,590 A | 4/1989 | Stancik, Jr. |

(Continued)

FOREIGN PATENT DOCUMENTS

| | | |
|---|---|---|
| CN | 1899222 A | 1/2007 |
| CN | 101257860 A | 9/2008 |

(Continued)

OTHER PUBLICATIONS

Ai-Fakih E., et al., "The Use of Fiber Bragg Grating Sensors in Biomechanics and Rehabilitation Applications: The State-of-the-Art and Ongoing Research Topics," Sensors, Sep. 25, 2012, vol. 12, No. 10, pp. 12890-12926.
(Continued)

*Primary Examiner* — Nicholas W Woodall

(57) ABSTRACT

Spinal device/implants are provided, comprising a spinal device/implant and a sensor.

14 Claims, 23 Drawing Sheets

Related U.S. Application Data continuation of application No. 15/320,284, filed as application No. PCT/US2015/037825 on Jun. 25, 2015, now abandoned.

(60) Provisional application No. 62/017,106, filed on Jun. 25, 2014.

(51) Int. Cl.

| | |
|---|---|
| *A61B 5/03* | (2006.01) |
| *A61B 17/00* | (2006.01) |
| *A61B 17/70* | (2006.01) |
| *A61B 17/80* | (2006.01) |
| *A61B 90/00* | (2016.01) |
| *A61F 2/46* | (2006.01) |
| *A61F 2/30* | (2006.01) |
| *G16H 20/40* | (2018.01) |
| *G16H 40/67* | (2018.01) |

(52) U.S. Cl.
CPC .... *A61F 2002/30985* (2013.01); *G16H 20/40* (2018.01); *G16H 40/67* (2018.01)

(56) References Cited

U.S. PATENT DOCUMENTS

| | | | |
|---|---|---|---|
| 4,858,620 A | 8/1989 | Sugarman et al. | |
| 4,862,878 A | 9/1989 | Davison et al. | |
| 5,197,488 A * | 3/1993 | Kovacevic | A61F 2/38 600/595 |
| 5,437,617 A | 8/1995 | Heinz et al. | |
| 5,484,389 A | 1/1996 | Stark et al. | |
| 5,593,409 A * | 1/1997 | Michelson | A61F 2/30744 606/247 |
| 5,672,954 A | 9/1997 | Watanabe | |
| 5,733,292 A * | 3/1998 | Gustilo | A61B 17/025 606/88 |
| 5,833,603 A | 11/1998 | Kovacs et al. | |
| 6,053,882 A | 4/2000 | Johansen | |
| 6,245,109 B1 | 6/2001 | Mendes et al. | |
| 6,447,448 B1 * | 9/2002 | Ishikawa | A61B 5/036 600/377 |
| 6,565,573 B1 | 5/2003 | Ferrante et al. | |
| 6,610,101 B2 | 8/2003 | Herr et al. | |
| 6,706,071 B1 | 3/2004 | Wolter | |
| 6,908,466 B1 | 6/2005 | Bonutti et al. | |
| 7,009,511 B2 | 3/2006 | Mazar et al. | |
| 7,044,951 B2 | 5/2006 | Medoff et al. | |
| 7,097,662 B2 | 8/2006 | Evans, III et al. | |
| 7,127,300 B2 | 10/2006 | Mazar et al. | |
| 7,130,695 B2 | 10/2006 | Czygan et al. | |
| 7,383,071 B1 | 6/2008 | Russell et al. | |
| 7,450,332 B2 | 11/2008 | Pasolini et al. | |
| 7,463,997 B2 | 12/2008 | Pasolini et al. | |
| 7,491,188 B2 | 2/2009 | Holman et al. | |
| 7,559,951 B2 | 7/2009 | DiSilvestro et al. | |
| 7,686,808 B2 | 3/2010 | Orbay et al. | |
| 7,789,897 B2 | 9/2010 | Sanders | |
| 7,811,311 B2 | 10/2010 | Markworth et al. | |
| 7,889,070 B2 | 2/2011 | Reeves et al. | |
| 7,905,924 B2 | 3/2011 | White | |
| 7,924,267 B2 | 4/2011 | Sirtori | |
| 8,029,566 B2 | 10/2011 | Lozier et al. | |
| 8,048,134 B2 | 11/2011 | Partin | |
| 8,083,741 B2 | 12/2011 | Morgan et al. | |
| 8,172,905 B2 | 5/2012 | Baynham et al. | |
| 8,176,922 B2 | 5/2012 | Sherman et al. | |
| 8,226,723 B2 | 7/2012 | Conti et al. | |
| 8,244,368 B2 | 8/2012 | Sherman | |
| 8,283,793 B2 | 10/2012 | Pless | |
| 8,303,663 B2 | 11/2012 | Jimenez et al. | |
| 8,311,632 B2 | 11/2012 | Pless et al. | |
| 8,343,223 B2 | 1/2013 | Bucci | |
| 8,361,121 B2 | 1/2013 | Barry | |
| 8,361,131 B2 | 1/2013 | Chin et al. | |
| 8,372,420 B2 | 2/2013 | Hunter et al. | |
| 8,486,070 B2 | 7/2013 | Morgan et al. | |
| 8,556,888 B2 | 10/2013 | Nields et al. | |
| 8,634,928 B1 | 1/2014 | O'Driscoll et al. | |
| 8,663,287 B2 | 3/2014 | Butler et al. | |
| 8,728,160 B2 | 5/2014 | Globerman et al. | |
| 9,019,098 B2 | 4/2015 | Okano | |
| 9,095,436 B2 * | 8/2015 | Boyden | A61B 17/68 |
| 9,445,930 B2 | 9/2016 | Chen et al. | |
| 9,456,915 B2 | 10/2016 | Chen et al. | |
| 9,629,583 B2 | 4/2017 | Gradel et al. | |
| 10,070,973 B2 | 9/2018 | Sherman et al. | |
| 10,219,699 B2 | 3/2019 | Wilder et al. | |
| 10,285,637 B1 | 5/2019 | Hnat et al. | |
| 10,499,855 B2 | 12/2019 | Hunter | |
| 10,582,896 B2 | 3/2020 | Revie et al. | |
| 10,925,537 B2 | 2/2021 | Bailey et al. | |
| 2002/0024450 A1 | 2/2002 | Townsend et al. | |
| 2002/0026226 A1 | 2/2002 | Ein | |
| 2002/0049394 A1 | 4/2002 | Roy et al. | |
| 2002/0147416 A1 | 10/2002 | Zogbi et al. | |
| 2003/0069644 A1 | 4/2003 | Kovacevic et al. | |
| 2003/0088385 A1 | 5/2003 | David | |
| 2003/0196352 A1 | 10/2003 | Bledsoe et al. | |
| 2003/0204267 A1 | 10/2003 | Hazebrouck et al. | |
| 2004/0011137 A1 | 1/2004 | Hnat et al. | |
| 2004/0019382 A1 | 1/2004 | Amirouche et al. | |
| 2004/0019384 A1 | 1/2004 | Kirking et al. | |
| 2004/0204766 A1 | 10/2004 | Siebel | |
| 2004/0211580 A1 | 10/2004 | Wang et al. | |
| 2004/0243148 A1 | 12/2004 | Wasielewski | |
| 2004/0249464 A1 | 12/2004 | Bindseil et al. | |
| 2004/0249471 A1 | 12/2004 | Bindseil et al. | |
| 2005/0010299 A1 | 1/2005 | Disilvestro | |
| 2005/0012610 A1 | 1/2005 | Liao et al. | |
| 2005/0021126 A1 | 1/2005 | Machan et al. | |
| 2005/0065408 A1 | 3/2005 | Benderev | |
| 2005/0149173 A1 | 7/2005 | Hunter et al. | |
| 2005/0152945 A1 | 7/2005 | Hunter et al. | |
| 2005/0165317 A1 | 7/2005 | Turner et al. | |
| 2005/0187639 A1 | 8/2005 | Hunter et al. | |
| 2005/0228410 A1 | 10/2005 | Berreklouw | |
| 2005/0234555 A1 * | 10/2005 | Sutton | A61F 2/4425 623/18.12 |
| 2005/0242666 A1 | 11/2005 | Huscher et al. | |
| 2005/0245992 A1 | 11/2005 | Persen et al. | |
| 2005/0273170 A1 * | 12/2005 | Navarro | A61F 2/442 600/595 |
| 2006/0009856 A1 | 1/2006 | Sherman et al. | |
| 2006/0024773 A1 | 2/2006 | Ohmiya et al. | |
| 2006/0030771 A1 | 2/2006 | Levine et al. | |
| 2006/0030945 A1 | 2/2006 | Wright | |
| 2006/0036246 A1 | 2/2006 | Carl et al. | |
| 2006/0047283 A1 | 3/2006 | Evans, III et al. | |
| 2006/0052782 A1 | 3/2006 | Morgan et al. | |
| 2006/0079824 A1 | 4/2006 | Munch-Fals et al. | |
| 2006/0079836 A1 | 4/2006 | Holman et al. | |
| 2006/0100508 A1 | 5/2006 | Morrison | |
| 2006/0111777 A1 | 5/2006 | Chen | |
| 2006/0142670 A1 | 6/2006 | DiSilvestro et al. | |
| 2006/0184067 A1 | 8/2006 | Clark et al. | |
| 2006/0224088 A1 | 10/2006 | Roche | |
| 2006/0229730 A1 | 10/2006 | Railey et al. | |
| 2006/0247773 A1 | 11/2006 | Stamp | |
| 2006/0271112 A1 | 11/2006 | Martinson et al. | |
| 2006/0271199 A1 | 11/2006 | Johnson | |
| 2006/0282168 A1 | 12/2006 | Sherman et al. | |
| 2007/0004994 A1 | 1/2007 | Sherman | |
| 2007/0005141 A1 | 1/2007 | Sherman | |
| 2007/0049933 A1 | 3/2007 | Ahn et al. | |
| 2007/0088442 A1 | 4/2007 | Cima et al. | |
| 2007/0089518 A1 | 4/2007 | Ericson et al. | |
| 2007/0100449 A1 | 5/2007 | O'Neil et al. | |
| 2007/0118243 A1 | 5/2007 | Schroeder et al. | |
| 2007/0179739 A1 | 8/2007 | Donofrio et al. | |
| 2007/0233065 A1 | 10/2007 | Donofrio et al. | |
| 2007/0233267 A1 | 10/2007 | Amirouche et al. | |
| 2007/0234819 A1 | 10/2007 | Amirouche et al. | |

(56) References Cited

U.S. PATENT DOCUMENTS

| | | |
|---|---|---|
| 2007/0238992 A1 | 10/2007 | Donofrio et al. |
| 2007/0239282 A1 | 10/2007 | Caylor et al. |
| 2007/0265662 A1 | 11/2007 | Ufford |
| 2008/0027679 A1 | 1/2008 | Shklarski |
| 2008/0033527 A1 | 2/2008 | Nunez et al. |
| 2008/0065225 A1 | 3/2008 | Wasielewski et al. |
| 2008/0076972 A1 | 3/2008 | Dorogusker et al. |
| 2008/0208516 A1 | 8/2008 | James |
| 2008/0215609 A1 | 9/2008 | Cleveland et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0306407 A1 | 12/2008 | Taylor |
| 2009/0005708 A1 | 1/2009 | Johanson et al. |
| 2009/0012372 A1 | 1/2009 | Burnett et al. |
| 2009/0048524 A1 | 2/2009 | Wildau et al. |
| 2009/0088756 A1 | 4/2009 | Anderson |
| 2009/0157146 A1 | 6/2009 | Linder et al. |
| 2009/0192533 A1 | 7/2009 | Dlugos, Jr. et al. |
| 2009/0198288 A1 | 8/2009 | Hoof et al. |
| 2009/0253587 A1 | 10/2009 | Fernandez |
| 2009/0254063 A1 | 10/2009 | Oepen et al. |
| 2009/0264894 A1 | 10/2009 | Wasielewski |
| 2009/0287255 A1 | 11/2009 | Erickson et al. |
| 2009/0299228 A1 | 12/2009 | Lozier et al. |
| 2009/0299327 A1 | 12/2009 | Tilson et al. |
| 2010/0023108 A1 | 1/2010 | Toner et al. |
| 2010/0037731 A1 | 2/2010 | Li |
| 2010/0042121 A1 | 2/2010 | Schneider et al. |
| 2010/0100011 A1* | 4/2010 | Roche .......... A61B 5/4528 623/20.14 |
| 2010/0145337 A1 | 6/2010 | Janna et al. |
| 2010/0152621 A1 | 6/2010 | Janna et al. |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0262160 A1 | 10/2010 | Boyden et al. |
| 2010/0285082 A1 | 11/2010 | Fernandez |
| 2010/0331663 A1 | 12/2010 | Stein |
| 2011/0004076 A1 | 1/2011 | Janna et al. |
| 2011/0004124 A1 | 1/2011 | Lessar et al. |
| 2011/0019595 A1 | 1/2011 | Magar et al. |
| 2011/0054272 A1 | 3/2011 | Derchak |
| 2011/0059234 A1 | 3/2011 | Byun et al. |
| 2011/0063094 A1 | 3/2011 | Meiertoberens et al. |
| 2011/0077736 A1 | 3/2011 | Rofougaran |
| 2011/0082393 A1 | 4/2011 | Bort |
| 2011/0087306 A1 | 4/2011 | Goossen |
| 2011/0092948 A1 | 4/2011 | Shachar et al. |
| 2011/0213221 A1 | 9/2011 | Roche |
| 2011/0288436 A1 | 11/2011 | Stone |
| 2011/0319755 A1 | 12/2011 | Stein et al. |
| 2012/0123498 A1 | 5/2012 | Gross |
| 2012/0123716 A1 | 5/2012 | Clark |
| 2012/0130687 A1 | 5/2012 | Otto et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232662 A1 | 9/2012 | Jansen et al. |
| 2012/0283781 A1 | 11/2012 | Arnin |
| 2013/0006367 A1 | 1/2013 | Bucci |
| 2013/0066426 A1 | 3/2013 | Martinson et al. |
| 2013/0079668 A1 | 3/2013 | Stein et al. |
| 2013/0079671 A1 | 3/2013 | Stein et al. |
| 2013/0079675 A1 | 3/2013 | Stein et al. |
| 2013/0079679 A1 | 3/2013 | Roche et al. |
| 2013/0123684 A1 | 5/2013 | Giuffrida et al. |
| 2013/0144379 A1 | 6/2013 | Najafi et al. |
| 2013/0158669 A1 | 6/2013 | Sungarian et al. |
| 2013/0197656 A1 | 8/2013 | Conrad |
| 2013/0215979 A1 | 8/2013 | Yakovlev et al. |
| 2013/0225949 A1 | 8/2013 | Roche |
| 2013/0231703 A1 | 9/2013 | Seme et al. |
| 2013/0252610 A1 | 9/2013 | Kim et al. |
| 2013/0270750 A1 | 10/2013 | Green |
| 2013/0329258 A1 | 12/2013 | Pettis et al. |
| 2013/0337256 A1 | 12/2013 | Farmer et al. |
| 2013/0338455 A1 | 12/2013 | Gradel et al. |
| 2014/0031063 A1 | 1/2014 | Park et al. |
| 2014/0034626 A1 | 2/2014 | Illston |
| 2014/0048970 A1 | 2/2014 | Batchelder et al. |
| 2014/0053956 A1 | 2/2014 | Etter et al. |
| 2014/0077421 A1 | 3/2014 | Minick |
| 2014/0085102 A1 | 3/2014 | McCormick |
| 2014/0135589 A1 | 5/2014 | Osorio |
| 2014/0256324 A1 | 9/2014 | Mohanty et al. |
| 2014/0275849 A1 | 9/2014 | Acquista |
| 2014/0275861 A1 | 9/2014 | Kroh et al. |
| 2014/0296663 A1 | 10/2014 | Boyden et al. |
| 2014/0328253 A1 | 11/2014 | Lee et al. |
| 2015/0238304 A1 | 8/2015 | Amraoui |
| 2016/0029952 A1 | 2/2016 | Hunter |
| 2016/0038087 A1 | 2/2016 | Hunter |
| 2016/0101281 A1 | 4/2016 | Chen |
| 2016/0128573 A1 | 5/2016 | Wilder et al. |
| 2016/0192878 A1 | 7/2016 | Hunter |
| 2016/0340177 A1 | 11/2016 | Takada |
| 2017/0035593 A1 | 2/2017 | Chen et al. |
| 2017/0119566 A1 | 5/2017 | Chen et al. |
| 2017/0138986 A1 | 5/2017 | Kern |
| 2017/0181825 A1 | 6/2017 | Hunter |
| 2017/0189553 A1 | 7/2017 | Hunter |
| 2017/0196478 A1 | 7/2017 | Hunter |
| 2017/0196499 A1 | 7/2017 | Hunter |
| 2017/0196508 A1 | 7/2017 | Hunter |
| 2017/0196509 A1 | 7/2017 | Hunter |
| 2018/0228428 A1 | 8/2018 | Anker et al. |
| 2018/0235546 A1 | 8/2018 | Hunter |
| 2019/0231555 A1 | 8/2019 | Neubardt |
| 2019/0247197 A1 | 8/2019 | Jagannathan et al. |
| 2020/0054215 A1 | 2/2020 | Roche |
| 2020/0155327 A1 | 5/2020 | Suh et al. |
| 2021/0077241 A1 | 3/2021 | Hunter |

FOREIGN PATENT DOCUMENTS

| | | |
|---|---|---|
| CN | 101495025 A | 7/2009 |
| CN | 101773387 A | 7/2010 |
| CN | 202036215 U | 11/2011 |
| CN | 102740803 A | 10/2012 |
| CN | 102885626 A | 1/2013 |
| CN | 103313661 A | 9/2013 |
| CN | 103458830 A | 12/2013 |
| CN | 103735303 A | 4/2014 |
| CN | 103957992 A | 7/2014 |
| DE | 4322619 C1 | 9/1994 |
| DE | 10342823 A1 | 4/2005 |
| EP | 1147751 A2 | 10/2001 |
| EP | 1382308 A2 | 1/2004 |
| EP | 1803413 A2 | 7/2007 |
| EP | 1814471 B1 | 3/2010 |
| JP | 2022128381 A | 9/2022 |
| WO | 0149222 A1 | 7/2001 |
| WO | 2005120203 A2 | 12/2005 |
| WO | 2006105098 A2 | 10/2006 |
| WO | 2006108065 A2 | 10/2006 |
| WO | 2006113394 A2 | 10/2006 |
| WO | 2008032316 A2 | 3/2008 |
| WO | 2008103181 A1 | 8/2008 |
| WO | 2009083049 A1 | 7/2009 |
| WO | 2010040034 A2 | 4/2010 |
| WO | 2011126706 A2 | 10/2011 |
| WO | 2012095784 A1 | 7/2012 |
| WO | 2013044160 A2 | 3/2013 |
| WO | 2013096664 A1 | 6/2013 |
| WO | 2013140147 A1 | 9/2013 |
| WO | 2013152751 A1 | 10/2013 |
| WO | 2013152805 A1 | 10/2013 |
| WO | 2013155500 A1 | 10/2013 |
| WO | 2013163585 A1 | 10/2013 |
| WO | 2013179017 A1 | 12/2013 |
| WO | 2014018100 A1 | 1/2014 |
| WO | 2014020085 A2 | 2/2014 |
| WO | 2014071135 A1 | 5/2014 |

(56) References Cited

FOREIGN PATENT DOCUMENTS

| | | | |
|---|---|---|---|
| WO | 2014071968 A1 | 5/2014 | |
| WO | 2014074947 A2 | 5/2014 | |
| WO | 2014081594 A1 | 5/2014 | |
| WO | 2014083277 A1 | 6/2014 | |
| WO | 2014085170 A1 | 6/2014 | |
| WO | 2014100795 A1 | 6/2014 | |
| WO | 2014144070 A1 | 9/2014 | |
| WO | 2014144107 A1 | 9/2014 | |
| WO | 2014209916 A1 | 12/2014 | |
| WO | 2015021807 A1 | 2/2015 | |
| WO | 2015200704 A1 | 12/2015 | |
| WO | 2015200707 A1 | 12/2015 | |
| WO | 2015200718 A1 | 12/2015 | |
| WO | 2015200720 A2 | 12/2015 | |
| WO | 2015200722 A2 | 12/2015 | |
| WO | 2015200723 A1 | 12/2015 | |

OTHER PUBLICATIONS

Chandrakasan A.P., et al., "Next Generation Micro-Power Systems," Symposium on VLSI Circuits Digest of Technical Papers, 2008, pp. 1-5, 04 pages.

Extended European Search Report for European Application No. 14817352.9, mailed Jun. 13, 2017, 15 Pages.

Extended European Search Report for European Application No. 15811139.3, mailed Aug. 9, 2018, 17 Pages.

Extended European Search Report for European Application No. 15811397.7, mailed Mar. 20, 2018, 13 Pages.

Extended European Search Report for European Application No. 15842678.3, mailed Feb. 5, 2019, 13 Pages.

Extended European Search Report for European Application No. 20171179.3, mailed Mar. 24, 2021, 18 Pages.

Graichen F., et al., "Hip Endoprosthesis for in Vivo Measurement of Joint Force and Temperature," Journal of biomechanics, 1999, vol. 32, No. 10, pp. 1113-1117.

International Preliminary Report on Patentability for International Application No. PCT/US2015/037825, mailed Jan. 5, 2017, 08 Pages.

International Preliminary Report on Patentability for International Application No. PCT/US2015/037827, mailed Jan. 5, 2017, 09 Pages.

International Preliminary Report on Patentability for International Application No. PCT/US2015/050789, mailed Mar. 30, 2017, 07 Pages.

International Search Report and Written Opinion for International Application No. PCT/US2014/028381, mailed Jul. 7, 2014, 15 Pages.

International Search Report and Written Opinion for International Application No. PCT/US2014/043736, mailed Oct. 15, 2014, 15 Pages.

International Search Report and Written Opinion for International Application No. PCT/US2015/037825, mailed Dec. 8, 2015, 10 pages.

International Search Report and Written Opinion for International Application No. PCT/US2015/037827, mailed Dec. 8, 2015, 23 Pages.

International Search Report and Written Opinion for International Application No. PCT/US2015/050789, mailed Feb. 1, 2016, 10 Pages.

Loh N.C., et al., "Sub-10 cm3 Interferometric Accelerometer with Nano-g Resolution," Journal of Microelectromechanical Systems, vol. 11, No. 3, Jun. 2002, pp. 182-187.

Partial European Search Report for European Application No. 20171179.3, mailed Nov. 10, 2020, 16 Pages.

Partial Supplementary European Search Report for European Application No. 14762650.1, mailed Mar. 17, 2017, 08 Pages.

Partial Supplementary European Search Report for European Application No. 15811139.3, mailed Mar. 12, 2018, 16 Pages.

Partial Supplementary European Search Report for European Application No. 15842678.3, mailed Oct. 16, 2018, 15 Pages.

Polla D.L., et al., "Microdevices in Medicine," Annual Review Of Biomedical Engineering, 2000, vol. 02, pp. 551-576.

Singh U.K., et al., "Piezoelectric Power Scavenging of Mechanical Vibration Energy," Australian Mining Technology Conference, Oct. 2-4, 2007, pp. 111-118.

Xiang X., et al., "A Review of the Implantable Electronic Devices in Biology and Medicine," China Academic Journal Electronic Publishing House, vol. 32 (3), Mar. 3, 2004, pp. 462-467.

Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.

Yiming L., et al., "Application of Wireless Sensor Networks in Healthcare," Chinese Journal of Medical Instrumentation, vol. 37 (5), Dec. 31, 2013, pp. 351-354 and Figure 1.

Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.

European Search Report for European Application No. 23160709.4, mailed May 12, 2023, 8 Pages.

* cited by examiner

△ Pressure Sensor  ☐ Contact Sensor
● Position Sensor / Location Marker  ☆ Chemical sensor △ Pressure Sensor  ☐ Contact Sensor
● Position Sensor / Location Marker  ☆ Chemical sensor

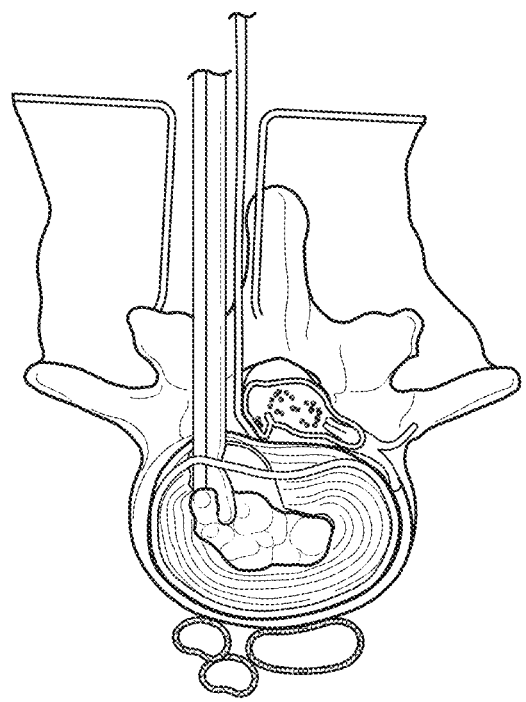
Fig. 18
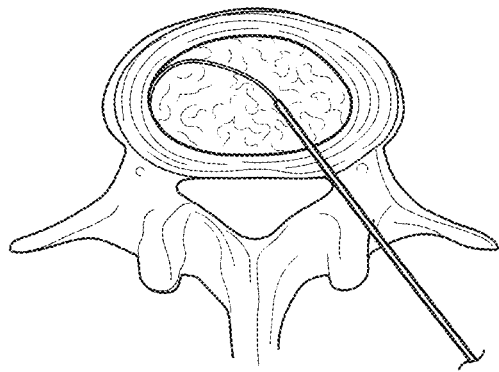 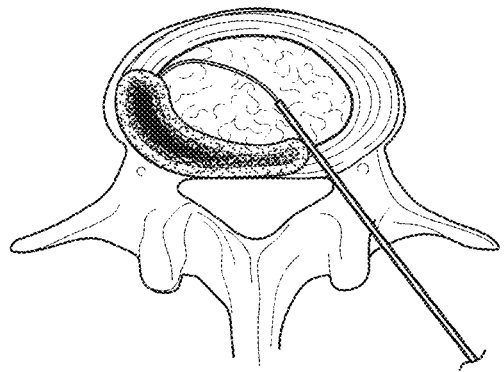
Fig. 19A  Fig. 19B

DEVICES, SYSTEMS AND METHODS FOR USING AND MONITORING SPINAL IMPLANTS

CROSS-REFERENCE TO RELATED APPLICATIONS

All applications for which a foreign or domestic priority claim is identified in the Application Data Sheet as filed with the present application are hereby incorporated by reference.

FIELD OF THE INVENTION

The present invention relates generally to spinal implants, and more specifically, to devices and methods for monitoring the placement, efficacy, and performance of a wide variety of spinal implants, including for example, in instruments that are utilized to operate on the spine, such as rods, vertebroplasty balloons, bone fillers and cements, screws (e.g., pedicle screws), spinal fusion devices (e.g., plates), spinal cages, and artificial discs.

BACKGROUND

The vertebral column, also known as the backbone or spine, has many functions, including for example, to provide support for the body, to provide protection for the spinal cord and associated nerves, to allow a body to be flexible, and to act as a shock absorber for bearing loads. For example, as shown in FIG. 1A, the spine consists of bony vertebrae 2, (see also FIG. 1C), and the intervertebral disc 4. The disc (FIG. 1B) has a strong, thick outer part (Annulus 5) and a gelatinous internal component (Nucleus Pulposis 3). Associated spinal nerve roots 6 can be seen exiting the spine between the bony vertebrae.

However, conditions affecting vertebrae and/or the vertebral discs can result in injury to the spinal cord and/or the spinal nerves (e.g., trauma, diseases of the vertebral body or intervertebral disc), resulting in serious complications such as severe pain, nerve damage, lower limb weakness, bowel and bladder dysfunction, paralysis and even death. Common conditions affecting the vertebral column include degenerative disc disease (herniated discs), osteoporosis (resulting in vertebral compression fractures), traumatic fracture, and various forms of spinal instability or deformation (e.g., scoliosis).

In order to lessen the effects of injury or disease, a wide variety of spinal implants, and instruments suitable for operating on the spine and/or delivering or implanting a spinal implant have been developed. Representative examples of spinal implants include rods, screws (e.g., pedicle screws), spinal fusion devices (e.g., plates), spinal cages, and artificial discs (see e.g.,: spinal cages (e.g., U.S. Pat. Nos. 5,425,772, 6,247,847, 6,428,575, 6,746,484, 7,722,674, 7,744,599, 7,988,713, 8,172,905, and U.S. Patent App. Nos. 2011/0015742, 2012/0046750, 2013/0053894, and 2013/0158669): pedicle screws and associated devices (e.g., U.S. Pat. Nos. 7,678,137, 8,361,121 and U.S. Patent App. Nos. 2005/0187548, 2006/0195086, 2008/0154309 and 2009/0287255); artificial discs and associated assemblies (e.g., U.S. Pat. Nos. 5,676,701, 8,226,723, and U.S. Patent App. Nos. 2006/0293753, 2007/0088439, 2007/0179611, 2008/0133014, 2011/0054617, and 2012/0232662); spinal rods and associated assemblies (e.g. U.S. Patent App. Nos. 2003/0050640, 2004/0015166, 2007/0118122, 2008/0306528, 2009/0177232, 2011/0245875, 2013/0211455, and 2013/0231703), and spinal plates and their assemblies (e.g., U.S. Pat. Nos. 8,246,664, 8,262,594, 8,343,223, and U.S. Patent App. Nos. 2009/0210008, 2010/0069968, and 2013/0006367)).

Unfortunately, when spinal surgery is performed or when a spinal implant is inserted, various complications may arise during the procedure (whether it is an open surgical procedure such as the placement of spinal fusion devices, cages or artificial discs, or minimally invasive procedures such as vertebroplasty, kyphoplasty or microdiscectomy). For example, during a procedure, the surgeon may wish to confirm correct anatomical alignment of the spinal column and/or implant and/or detect any abnormal motion between the spinal implant and the surrounding tissue so that corrective adjustments can be made during the procedure itself. In addition, to the extent the spinal device or implant is utilized in a surgical procedure, a physician may wish to confirm the correct placement of the device (such as a spinal fusion device, a spinal cage, an artificial discs) or implant (such as bone cement, synthetic polymers, bone tissue, bone matrix, bone growth factors), and confirm the delivery of it to its final, desired anatomical location. Post-procedure, the patient may experience neurological symptoms and pain if there is abnormal movement, migration of the device, breakage of the device, or in more serious cases infection, inflammation and/or pressure on the spinal cord and spinal nerves resulting from complications associated with the spinal implant.

The present invention discloses novel spinal implants which overcome many of the difficulties and limitations found with previous spinal devices and implants, methods for constructing and monitoring these novel spinal devices and implants, and further provides other related advantages.

SUMMARY

Briefly stated, spinal devices and implants (also referred to as 'medical devices') are provided comprising a spinal device or implant along with one or more sensors to monitor the integrity, function, location and efficaciousness of the spinal device or implant. The sensors may be positioned on the inside of the spinal device/implant, within the body of the spinal device/implant, or on the outer surface (or surfaces) of the spinal device/implant, and/or between the spinal device/implant and any device that might be utilized to deliver or secure the implant (e.g., a cement, adhesive, catheter, balloon catheter, or other medical device). Within certain embodiments, the sensors are of the type that are passive and thus do not require their own power supply.

According to various embodiments of the invention, the medical device comprises a spinal implant, along with one or more sensors. Examples of spinal devices and implants include pedicle screws, spinal rods, spinal wires, spinal plates, spinal cages, artificial discs, bone cement, growth factors (Bone Morphogenic Protein—BMP) as well as combinations of these (e.g., one or more pedicle screws and spinal rods, one or more pedicle screws and a spinal plate). In addition medical delivery devices for the placement of spinal devices and implants, along with one or more sensors, are also provided. Examples of medical delivery devices for spinal implants include kyphoplasty balloons, catheters (including thermal catheters and bone tunnel catheters), bone cement injection devices, microdiscectomy tools and other surgical tools. In addition, further components or compositions may be delivered along with the spinal implant and/or by the medical delivery device itself, and include fillers such as bone cement (PMMA), growth factors (such as BMP) and/or other polymers combined with one or more sensors.

Within preferred embodiments of the above, the medical device, spinal implant, medical delivery device and filler are all provided in a sterile form (e.g., ETO sterilized), and in a kit containing components suitable for a particular spinal surgery.

Representative examples of sensors suitable for use within the present invention include accelerometers (acceleration, tilt, vibration, shock and rotation sensors), pressure sensors, contact sensors, position sensors, chemical sensors, tissue metabolic sensors, mechanical stress sensors and temperature sensors. Within particularly preferred embodiments the sensor is a wireless sensor, or a sensor connected to a wireless microprocessor. Within further embodiments the spinal device, implant, delivery device or surgical tool can have more than one type of the above-noted sensors.

According to various embodiments, sensors are placed at different locations in the spinal device/implant in order to monitor the operation, movement, location, medical imaging (both of the spinal device/implant and the surrounding tissues), function, wear, performance, potential side effects, medical status of the patient and the medical status of the spinal device/implant and its interface with the live tissue of the patient. Live, continuous, in situ, monitoring of patient activity, patient function, spinal device/implant activity, spinal device/implant function, spinal device/implant performance, spinal device/implant placement, spinal device/implant forces and mechanical stresses, spinal device/implant and surrounding tissue anatomy (imaging), mechanical and physical integrity of the spinal device/implant, and potential local and systemic side effects is provided. In addition, information is available on many aspects of the spinal device/implant and its interaction with the patient's own body tissues, including clinically important measurements not currently available through physical examination, medical imaging and diagnostic medical studies.

According to one embodiment, the sensors provide evaluation data of any motion or movement of the spinal device/implant. Motion sensors and accelerometers can be used to accurately determine the movement of the spinal implant during surgical placement, during medical and physical examination post-operatively and during normal daily activities after the patient returns home.

According to another embodiment, contact sensors are provided between the spinal implant and the surrounding tissue and/or between articulated components of the device/implant itself. In other embodiments, vibration sensors are provided to detect the vibration between the spinal implant and the surrounding tissue and/or articulated components of the device/implant itself. Increases in vibration may indicate that the spinal implant is loosening from the surrounding tissue (or articulated device segments), which may result in damage to the body and/or lead to breakage or failure of the device. In other embodiments, strain gauges are provided to detect the strain between the spinal implant and the surrounding tissue and/or between articulated components of the device/implant itself. Sudden increases in strain may indicate that too much stress is being placed on the spinal implant, which may increase damage to the body and/or breakage and damage to the device.

According to other embodiments, accelerometers are provided which detect vibration, shock, tilt and rotation of the device/implant and by extension the surrounding tissue itself. According to other embodiments, sensors for measuring surface wear, such as contact or pressure sensors, may be embedded at different depths within the spinal device/implant in order to monitor contact of the spinal device/implant with surrounding tissues, or degradation of the spinal device/implant over time (e.g., in the context of a biodegradable or bioerodible implants and devices). In other embodiments, position sensors, as well as other types of sensors, are provided which indicate potential problems such as movement, migration, pressure on surrounding anatomical structures, alignment, breakage, cracking and/or bending of the spinal device/implant in actual use over a period of time.

Within further embodiments, the spinal device/implant can contain sensors at specified densities in specific locations. For example, the spinal device/implant can have a density of sensors of greater than one, two, three, four, five, six, seven, eight, nine, or ten sensors (e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these) per square centimeter of the device/implant. Within other embodiments, the spinal device/implant can have a density of sensors of greater than one, two, three, four, five, six, seven, eight, nine, or ten sensors (e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these) per cubic centimeter of the device.

Within certain embodiments of the invention, the spinal device/implant is provided with a specific unique identifying number, and within further embodiments, each of the sensors on, in or around the spinal device/implant each have either a specific unique identification number, or a group identification number (e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors). Within yet further embodiments, the specific unique identification number or group identification number is specifically associated with a position on, in or around the spinal device/implant.

Within other aspects of the invention methods are provided for monitoring an anatomically-implanted spinal device/implant comprising the steps of transmitting a wireless electrical signal from a location outside the body to a location inside the body; receiving the signal at a sensor positioned on, in or around a spinal device/implant located inside the body; powering the sensor using the received signal; sensing data at the sensor; and outputting the sensed data from the sensor to a receiving unit located outside of the body.

Within other aspects of the invention methods are provided for imaging a spinal device/implant as provided herein, comprising the steps of (a) detecting the location of one or more sensors in the spinal device/implant and any associated anatomical or radiological "landmarks" and/or associated medical delivery device or surgical tool; and (b) visually displaying the relative anatomical location of said one or more sensors, such that an image of the spinal implant is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper anatomical placement and functioning of the spinal device/implant. Particularly in spinal surgery, proper alignment and kyphosis (spinal curvature) are critical to obtaining a good outcome, therefore, allowing the surgeon to be able to see the implant's position in "real time" (particularly in procedures where direct vision is not possible) would be beneficial for achieving proper anatomical placement. Within other embodiments, the imaging techniques may be utilized post-operatively in order to examine the spinal device/implant, and/or to compare operation, integrity and/or movement of the device/implant over time.

The integrity of the spinal device/implant can be wirelessly interrogated and the results reported on a regular basis. This permits the health and status of the patient to be checked on a regular basis or at any time as desired by the patient and/or physician. Furthermore, the spinal implant can be wirelessly interrogated when signaled by the patient to do so (via an external signaling/triggering device) as part of "event recording"—i.e. when the patient experiences a particular event (e.g. pain, numbness, tingling, weakness, injury, instability, etc.) she/he signals/triggers the device/implant to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention, methods are provided for detecting and/or recording an event in a subject with one of the spinal device/implants provided herein, comprising the device/implant interrogation at a desired point in time. Within one aspect of the invention, methods are provided for detecting and/or recording an event in a subject with the spinal device/implant as provided herein, comprising the step of interrogating at a desired point in time the activity of one or more sensors within the spinal device/implant, and recording said activity. Within various embodiments, interrogation may be accomplished by the subject and/or by a health care professional. Within related embodiments, the step of recording may be performed with one or more wired devices, or, wireless devices that can be carried, or worn (e.g., a cellphone, watch or wristband, and/or glasses).

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensors [e.g., accelerometers (acceleration, tilt, vibration, shock and rotation sensors), pressure sensors, contact sensors, position sensors, chemical sensors, tissue metabolic sensors, mechanical stress sensors and temperature sensors] are constructed such that they may readily be incorporated into, or otherwise mechanically attached to, the spinal device/implant (e.g., by way of a an opening or other appendage that provides permanent attachment of the sensor to the spinal device/implant) and/or readily incorporated into body of the spinal device/implant.

Within yet other aspects of the invention methods, devices are provided suitable for transmitting a wireless electrical signal from a location outside the body to a location inside the body; receiving the signal at one of the aforementioned sensors positioned on, in or around the spinal device/implant located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the spinal device/implant, or on an associated device (e.g., an associated medical device, or an external device such as a cellphone, watch, wristband, and/or glasses. During a visit to the physician, the data can be downloaded via a wireless sensor, and the doctor is able to obtain data representative of real-time performance of the spinal implant, and any associated medical device.

The advantages obtained include more accurate monitoring of the spinal device/implant and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 9A is a posterolateral fusion (the bone graft is placed between the transverse processes of adjacent vertebrae) and FIG. 9B is an interbody fusion (the bone graft occurs between the bodies of the vertebrae in the space usually occupied by the intervertebral disc). Typically supporting devices (rods, screws, plates) are used as well (see FIG. 10).

FIG. 18 illustrates a common surgical procedure (microdiscectomy) wherein a portion of a herniated disc is removed endoscopically.

FIGS. 19A and 19B illustrate insertion of an electrothermal catheter (IDET—intradiscal electrothermal annuloplasty) into the diseased intervertebral disc, followed by heating of the tip of the thermal catheter, as shown in FIG. 19B to repair the weakened part of the annulus.

DETAILED DESCRIPTION OF THE INVENTION

Figure 1A:
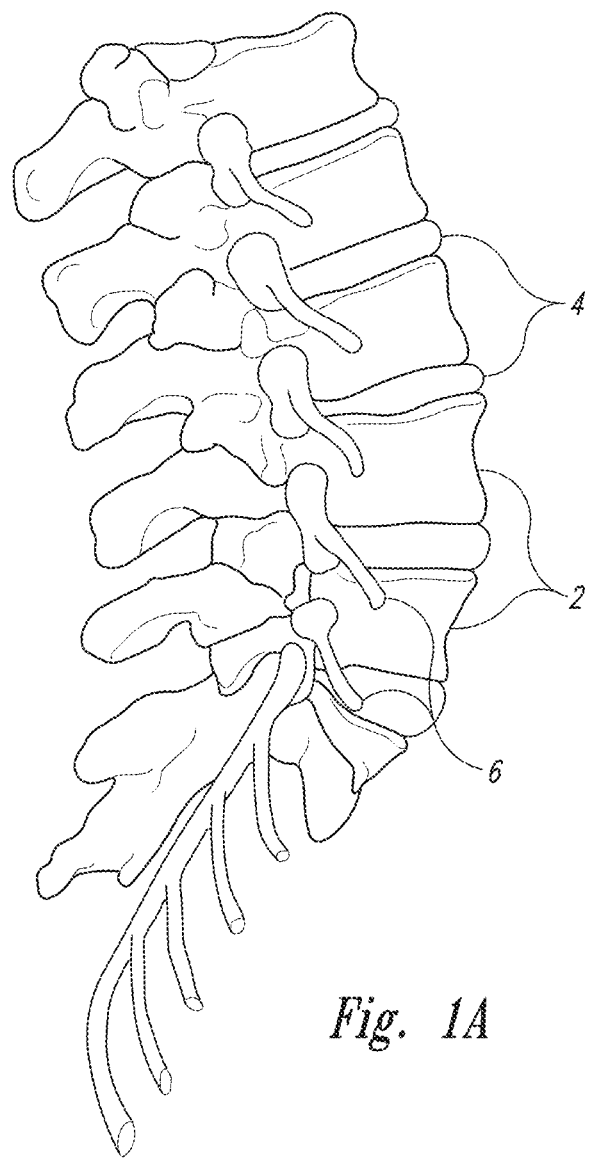
FIGS. 1A, 1B and 1C illustrate various portions of the spinal column, including a portion of a spine (FIG. 1A), an intervertebral disc (FIG. 1B), and a bony vertebra (FIG. 1C).

Briefly stated, the present invention provides a variety of spinal devices and implants that can be utilized to monitor the placement, location, anatomy, performance, integrity and/or efficaciousness of the spinal device/implant, and any associated medical devices and or device delivery instruments. Prior to setting forth the invention however, it may be helpful to an understanding thereof to first set forth definitions of certain terms that are used hereinafter.

"Spinal device and or Spinal implant" as those terms are utilized herein, refers to a wide variety of devices (typically hardware) and implants (typically biomaterials like bone cement and bone grafts) that can be implanted into, around, or in place of part of a subject's spine (typically in an interventional or surgical procedure), and which can be utilized to facilitate vertebral body fracture repair, fusion of vertebrae, correct degenerative disc disease (DDD), to stabilize the spinal column, and to correct deformities due to disease and/or injury. Spinal devices/implants are typically permanent, but in some cases may be temporary. Representative examples of spinal devices and implants include, for example: spinal cages (e.g., U.S. Pat. Nos. 5,425,772, 6,247,847, 6,428,575, 6,746,484, 7,722,674, 7,744,599, 7,988,713, 8,172,905, and U.S. Patent App. Nos. 2004/0082953, 2011/0015742, 2012/0046750, 2013/0053894, and 2013/0158669); pedicle screws and associated devices (e.g., U.S. Pat. Nos. 7,678,137, 8,361,121 and U.S. Patent App. Nos. 2005/0187548, 2006/0195086, 2008/0154309 and 2009/0287255); artificial discs and associated assemblies (e.g., U.S. Pat. Nos. 5,676,701, 8,226,723, and U.S. Patent App. Nos. 2006/0293753, 2007/0088439, 2007/0179611, 2008/0133014, 2011/0054617, and 2012/0232662); spinal rods and associated assemblies (e.g. U.S. Patent App. Nos. 2003/0050640, 2004/0015166, 2007/0118122, 2008/0306528, 2009/0177232, 2011/0245875, 2013/0211455, and 2013/0231703), spinal plates and their assemblies (e.g., U.S. Pat. Nos. 8,246,664, 8,262,594, 8,343,223, and U.S. Patent App. Nos. 2009/0210008, 2010/0069968, and 2013/0006367); and vertebroplasty/kyphoplasty balloons and bone cement (see e.g., US 2007/0100449, US 2009/0299373); all of which are incorporated by reference in their entirety.

Spinal device/implants may be composed of a wide variety of materials (including for example metals such as titanium, titanium alloys, and/or stainless steel), although other materials can also be utilized, including polymers (e.g., polymethylmethacrylate or "PMMA", poly-ether-ether-ketone or "PEEK" for cervical cages and anterior thoracolumbar implants, and bone graft material that can be allographic, xenographic or synthetic); and non-polymeric materials such as silicon nitride.

"Spinal Implant Surgical Device" or "Spinal Implant Delivery Device" refers to devices that can be utilized to introduce a spinal implant into a patient, and/or to surgical tools and devices that can be utilized to operate on the spine. Representative examples include guidewires, trocars, bone tunnel catheters, electrothermal catheters, endoscopes, microsurgical instruments, surgical instruments, kyphoplasty balloons, and bone cement injection devices to name a few.

The medical devices, implants and kits provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

"Sensor" refers to a device that can be utilized to measure one or more different aspects of a body tissue (anatomy, physiology, metabolism, and/or function), one or more aspects of the spinal device/implant, and one or more aspects of an associated medical device (e.g., screws, rods, hooks and wires) inserted within a body. Representative examples of sensors suitable for use within the present invention include, for example, fluid pressure sensors, contact sensors, position sensors, pulse pressure sensors, blood or fluid volume sensors, blood or fluid flow sensors, chemistry sensors (e.g., for cerebrospinal fluid—CSF, interstitial fluid, blood and/or other fluids), metabolic sensors (e.g., for cerebrospinal fluid—CSF, interstitial fluid, blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on the inside of the spinal device/implant, within the body of the spinal/device implant, on the outer surface (or surfaces) of the spinal device/implant, between the spinal implant and any device that might carry or deliver it (e.g., a delivery device, injection device, or surgical instrument) or be associated with it (e.g., screws, rods, hooks and wires). When the phrase "placed in the spinal implant" is utilized, it should be understood to refer to any of the above embodiments (or any combination thereof) unless the context of the usage implies otherwise.

The sensors may be placed in the spinal device/implant alone, or in the context of associated medical devices (e.g., screws, rods, hooks and wires), or in the context of a kit (e.g., a kit containing a delivery device, spinal device/implant, and/or associated devices suitable for a desired surgical procedure.). For example, within certain embodiments, the spinal device/implant, medical device or kit comprises sensors at a density of greater than 1, 2, 3, 4, 5, 6, 7, 8, 9, 10 or greater than 10 sensors per square centimeter. Within other aspects, the spinal device/implant, medical device or kit comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the spinal device/implant, medical device, or kit as described herein.

In various embodiments, the sensors may be placed within specific locations and/or randomly throughout the spinal device/implant and/or associated devices. In addition, the sensors may be placed in specific patterns (e.g., they may be arranged in the pattern of an X, as oval or concentric rings around the spinal implant and/or associated devices.

A. Representative Embodiments of Spinal Device/Implants and Medical Uses of Sensor-Containing Spinal Device/Implants In order to further understand the various aspects of the invention provided herein, the following sections are provided below: A. Spinal device/implants and their Use; B. Use of Spinal device/implants to Deliver Therapeutic Agent(s); C. Methods for Monitoring Infection in Spinal device/implants; D. Further Uses of Sensor-containing Spinal device/implants in Healthcare; E. Generation of Power from Spinal device/implants; F. Medical Imaging and Self-Diagnosis of Assemblies Comprising Spinal device/implants, Predictive Analysis and Predictive Maintenance; G. Methods of Monitoring Assemblies Comprising Spinal device/implants; and H. Collection, Transmission, Analysis, and Distribution of Data from Assemblies Comprising Spinal device/implants.

Spinal Device/Implants and their Use

A1. Vertebroplasty and Kyphoplasty Procedures

As noted above, within various aspects of the invention spinal device/implants and associated medical devices are provided for use in a wide variety of vertebroplasty and kyphoplasty procedures. Briefly, vertebral compression fractures can result from the sudden collapse of the vertebral body, and result in the rapid onset of back pain, numbness, tingling, weakness, spinal cord compression, and cauda equina syndrome (e.g., extremity weakness, paraplegia, urinary retention, urinary/fecal incontinence, sexual dysfunction, sciatica, decreased ankle reflex, and saddle anesthesia). It is typically found in patients with osteoporosis, but can occur due to other causes (e.g., trauma, lytic lesions from metastatic or primary tumors, infections, and osteogenesis imperfecta).

Figure 3A:
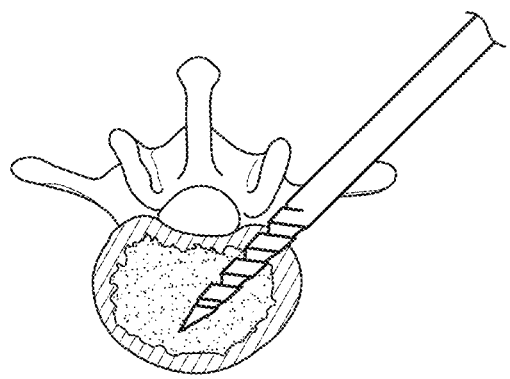
FIGS. 3A, 3B, 3C and 3D illustrate one embodiment called vertebroplasty wherein bone cement is injected directly within the body of the vertebrae (without the use of a balloon). These Figures illustrate one embodiment wherein, a hole is created in the vertebral body (FIG. 3A) through a bone tunneling catheter, followed by introduction of a delivery device (FIG. 3B) which allows injection of the bone cement directly into the collapsed bone. The compression fracture is corrected and supported through the injection of bone cement into the vertebral body (as shown in FIGS. 3C and 3D) to restore the normal height of the vertebra.
Figure 3B:
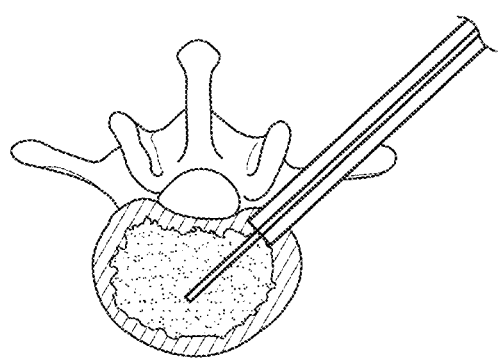
Figure 3C:
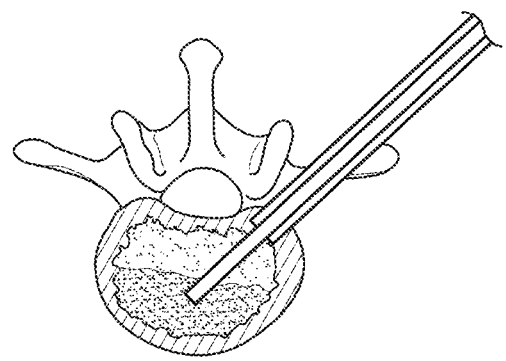
Figure 3D:
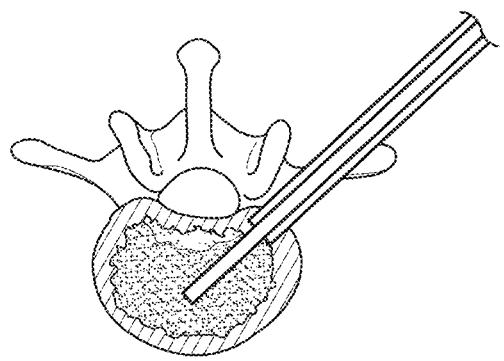

For vertebroplasty procedures, bone cement (e.g., polymethylmethacrylate or "PMMA") is injected percutaneously into the fractured vertebral body (see e.g., FIGS. 3C and 3D) in order restore normal vertebral height and anatomy so as to relieve the pain and symptoms associated with compression. Using a percutaneous approach or a small surgical incision, a hole is created in the wall of the vertebral body (FIG. 3A) by a specialized bone tunneling catheter, a delivery catheter is advanced into the vertebral body at the site of the fracture (FIG. 3B), and bone cement is injected (as shown in FIGS. 3C and 3D) into the cancellous bone within the vertebral body. The cement is allowed to infiltrate the cancellous bone of the collapsed vertebral body (FIG. 3C) until sufficient PMMA material has been injected to restore the vertebra to its normal height (FIG. 3D) and anatomy (the cement hardens and supports the fractured bone).

Figure 2A:
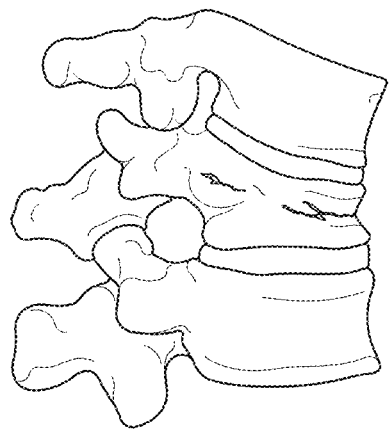
FIGS. 2A, 2B, 2C and 2D illustrate the repair of a compression fracture in a vertebral body (typically due to osteoporosis) through a form of vertebroplasty known as kyphoplasty. A balloon (200) is first inserted into the collapsed vertebral body (FIG. 2B) via a bone tunneling catheter and then inflated (FIG. 2C) in order to create a void in the cancellous bone and restore normal vertebral height and shape (kyphosis). PMMA (polymethylmethacrylate or bone cement—201) is then injected into the void, and allowed to harden in order to form a permanent support structure in the vertebrae (see FIG. 2D).
Figure 2B:
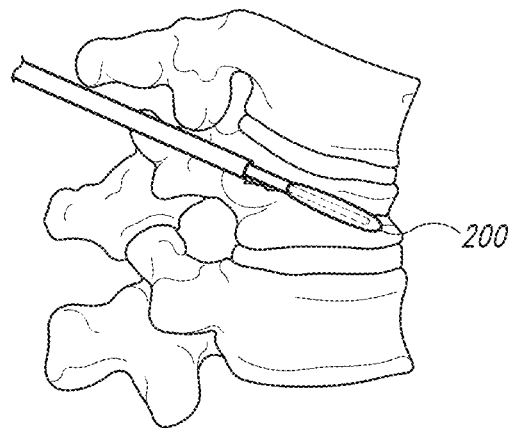
Figure 2C:
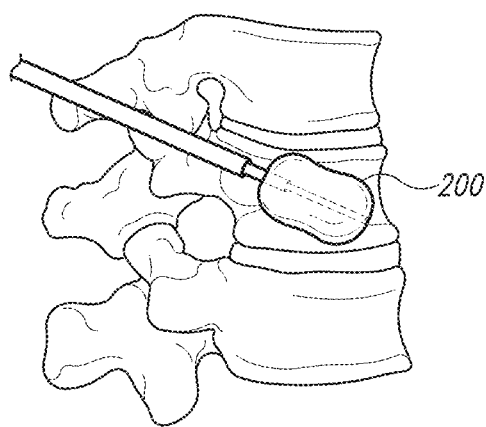
Figure 2D:
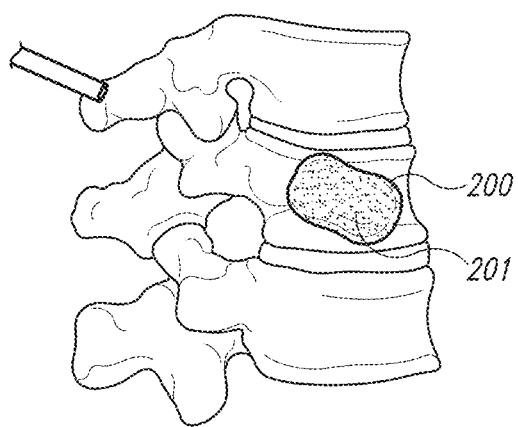

Kyphoplasty is a specialized form of vertebroplasty. In kyphoplasty procedures, a balloon is first inserted (FIG. 2B) into the cancellous bone of the vertebral compression fracture and then inflated (FIG. 2C) in order to restore normal vertebral height and spinal shape (kyphosis) and to create a void. The balloon is then removed and PMMA is injected into the void created by the balloon and allowed to harden in place to form a solid support structure in the vertebrae (see FIG. 2D).

Figure 4:
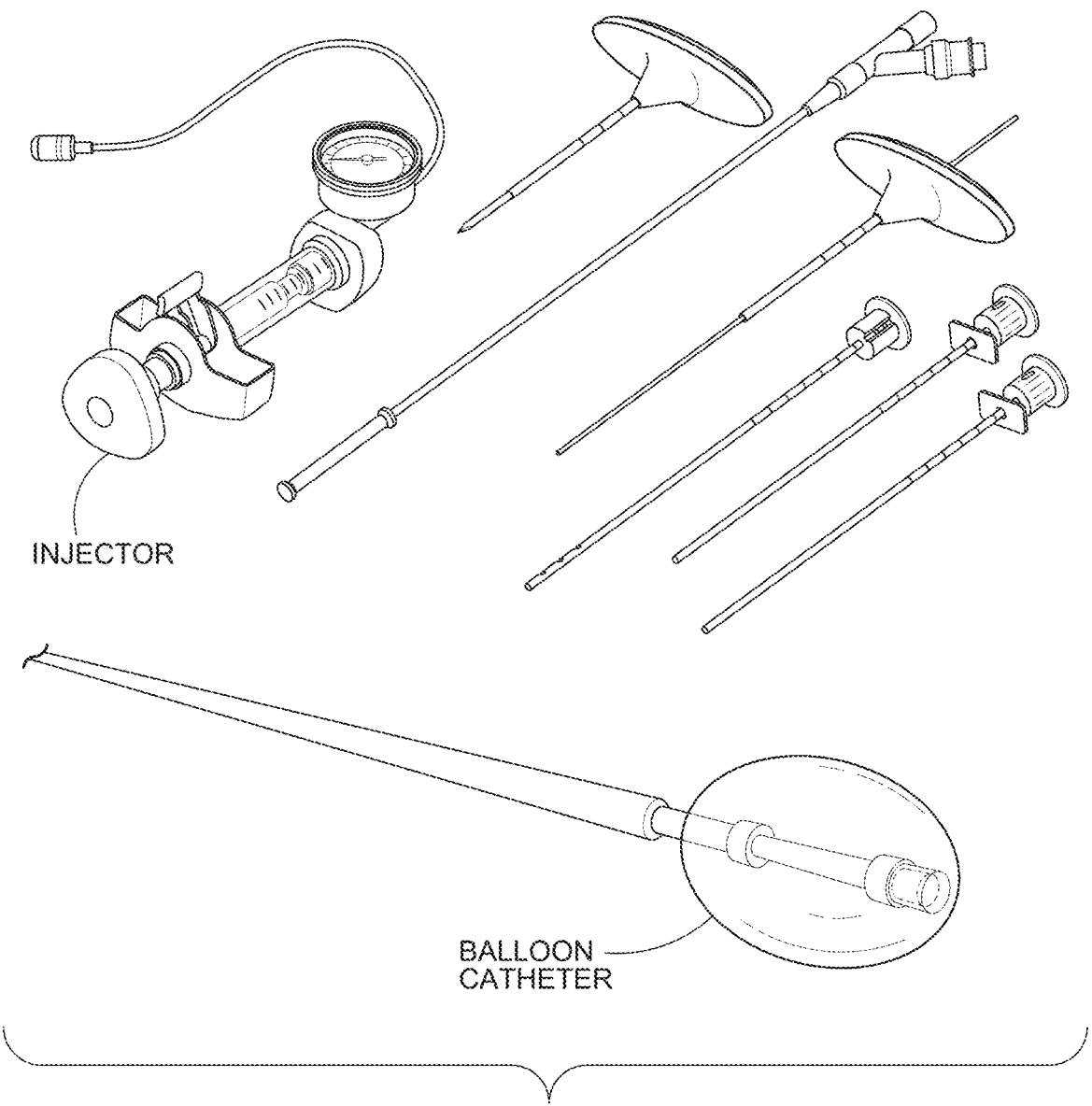
FIG. 4 illustrates a variety of medical instruments that can be utilized to assist in the preparation for vertebroplasty and kyphoplasty, including guidewires, trochars, bone tunnel catheters, kyphoplasty balloons, and an injector for the bone cement.

As shown in FIG. 4, a number of medical instruments can be utilized to complete a kyphoplasty, including, an introducing needle, an injector for the bone cement, bone needles, guidewires, bone tunnel catheters, balloon introducing catheters and a kyphoplasty balloon catheter.

Figure 5:
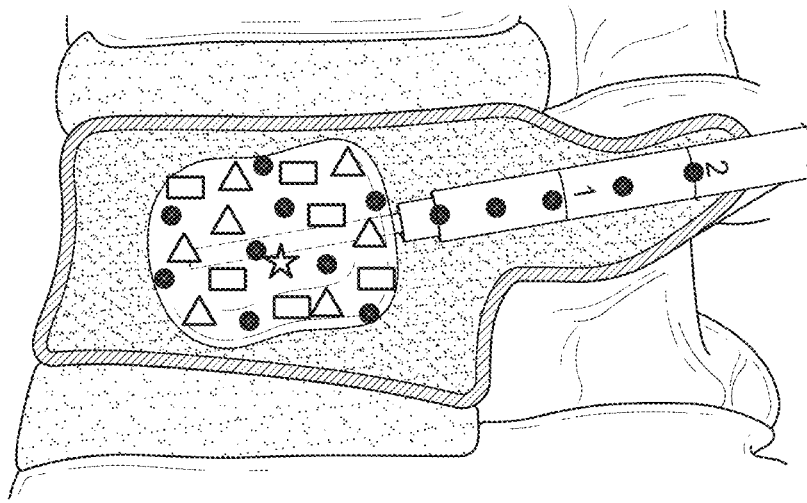
FIG. 5 illustrates one embodiment wherein a variety of sensors are placed on and/or within a kyphoplasty balloon.

Within various embodiments of the invention, sensors may be placed in some or all of the spinal implants and associated devices used for vertebroplasty and kyphoplasty. For example, as shown in FIG. 5, a variety of sensors can be placed on, or within the kyphoplasty balloon. For example, pressure sensors (designated by an open triangle) may be distributed throughout the balloon in order to monitor pressure exerted on the cancellous bone by the kyphoplasty balloon (particularly during inflation) and to optimize the inflation pressure (preventing over-inflation leading to potential tissue damage) and deflation pressure (ensuring the balloon is fully deflated before attempting to remove the device). Contact sensors (designated as an open rectangle) may also be distributed throughout the balloon in order to monitor contact between the balloon and the cancellous bone of the vertebral body. Position sensors/location markers (designated as a solid circle) may be distributed throughout the balloon (as well as on placement devices such as the introducers or bone tunnel catheters) in order to assist in accurate placement of the insertion device, the balloon, and bone cement into the compression fracture. Position sensors and location markers are also useful to monitor the expansion of the vertebral body (by, for example monitoring the position of the balloon walls as the balloon is progressively inflated) to achieve a more precise expansion; one that can be more accurately matched to the anatomical deficit present. "Visualization" via the sensors present on the balloon assist with accurate placement, optimum expansion, more precise measurement of deficit correction and safe deflation and extraction; all completed in "real time" during the procedure. Chemical sensors (indicated by the star) may also be utilized, along with temperature sensors (not shown).

The sensors may have a variety of additional uses, including to assist in identifying vertebral anatomy (e.g., to measure the exact vertebral height restored and proper kyphosis during kyphoplasty), to prevent accidental placement of the kyphoplasty instruments into surrounding tissues (the spinal cord, spinal nerves, etc.), to confirm full (or optimal) balloon inflation and deflation, to confirm restoration of vertebral height and kyphosis after kyphoplasty, and to image the void where bone cement will be injected, to more precisely match the volume to be injected, and to prevent overfilling and/or leakage of the bone cement.

Figure 6:
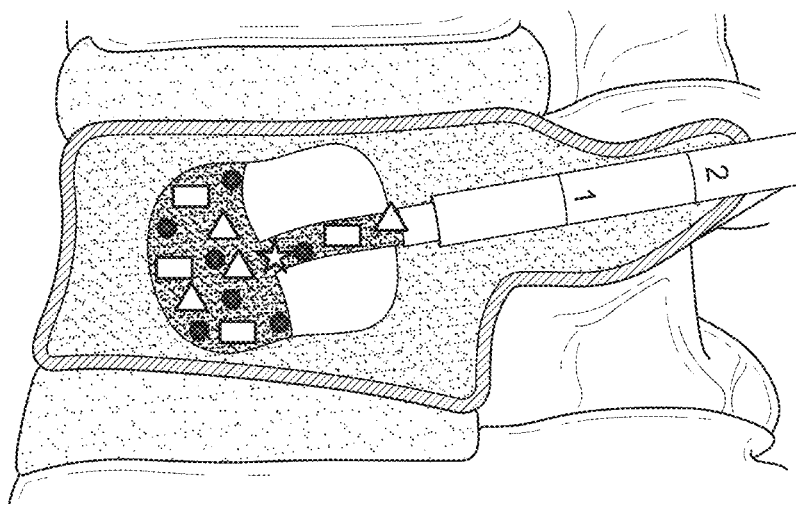
FIG. 6 illustrates one embodiment wherein the filler (typically bone cement) administered into the vertebral compression fracture contains a variety of sensors.

Similarly, as shown in FIG. 6, one or more sensors may be placed within the bone cement (and hence injected into the vertebral body). For example, contact sensors (shown as the open rectangle) may be distributed throughout the bone cement in order to monitor contact with the vertebral body, and to detect any loosening that might occur between the bone cement and the surrounding bone (particularly after hardening and during post-operative follow-up). Pressure sensors (shown as open triangles) may be distributed throughout the bone cement to detect any areas of excessive pressure, either due to improper injection at the time of placement, or due to shifting or further bone collapse in the post-operative follow-up. One or more position sensors and/or location sensors (shown as the solid circles) may be included within the bone cement in order to assist in accurate placement of the cement, to provide for correct filling (but not overfilling), to avoid or detect possible leaks into the spinal canal or adjacent spinal nerves, and to maintain the correct vertebral height and spinal kyphosis. Post-operatively, the sensors can be utilized to assess maintenance of vertebral anatomy, to monitor and image the placement, size and volume of the cement over time, and to determine the exact cement location (including any possible migration, dissolution, resorption, leakage, impingement against the spinal cord or spinal nerves, and/or embolization; such as to the lungs or elsewhere).

As is also shown in FIG. 6, chemical sensors can be utilized to monitor pH, calcium content, and other parameters (e.g., in order to predict and/or monitor the progression of osteoporosis, tumor growth and/or bone metabolism). Similarly, temperature sensors (not shown), can be utilized to monitor the temperature of the cement (the cement is above body temperature when initially inserted before hardening), as well as indicate any possible early signs of inflammation or infection.

Accelerometers (not shown in FIG. 6) may also be distributed through the bone cement in order to detect acceleration, vibration, shock, tilt and rotation of the cement within the vertebral body. Such sensors may be utilized to create 2D and 3D imaging data which show the size and shape of the filled void, movement and/or dissolution of the bone cement, and leakage or impingement of the cement into the spinal cord and/or around the spinal nerves. Within preferred embodiments the image data can be collected over time, in order to visually show changes (e.g., a "movie" or "moving images") detected by the sensors.

In vertebroplasty, the bone cement is injected directly into the fracture without the creation of a void (See FIG. 3C, 3D). Because of this, the use of sensors within the injected bone cement (as described above and demonstrated in FIG. 6) to monitor pressure, location, position, contact and other measures (temperature, pH, etc.) during both placement and in subsequent follow-up is as, or more, important than as described for kyphoplasty. Once implanted the monitoring of sensor-containing bone cement is identical regardless of whether it is administered as part of vertebroplasty or kyphoplasty.

The above sensors may be continuously monitored in order to provide a 'real-world' range of motion for the spine, to assist in detecting any decrease in spinal health, to collect and compare procedure performance data over time, to evaluate patient function, and to better understand the conditions which implants are exposed to in the real world.

A2. Intervertebral Disc Disease/Spinal Fusion

Figure 7:
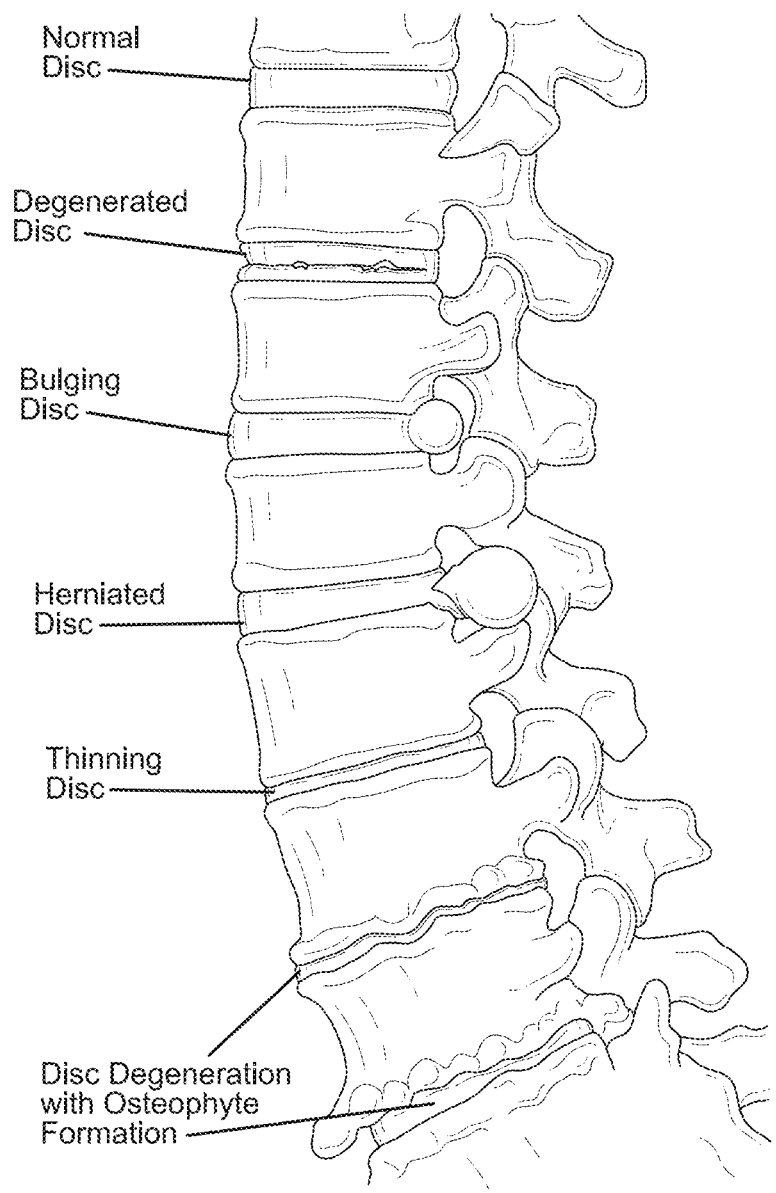
FIG. 7 illustrates a normal intervertebral disc, as well as various degenerative disc disease-related conditions.

Injury and/or disease of the intervertebral disc can result in substantive, chronic neck and/or back pain and/or neurological symptoms. Examples of chronic disc problems are shown in FIG. 7, which depicts a normal disc, degenerated disc, bulging disc, herniated disc, thinning disc, and disc degeneration with osteophyte formation.

Figure 9A:
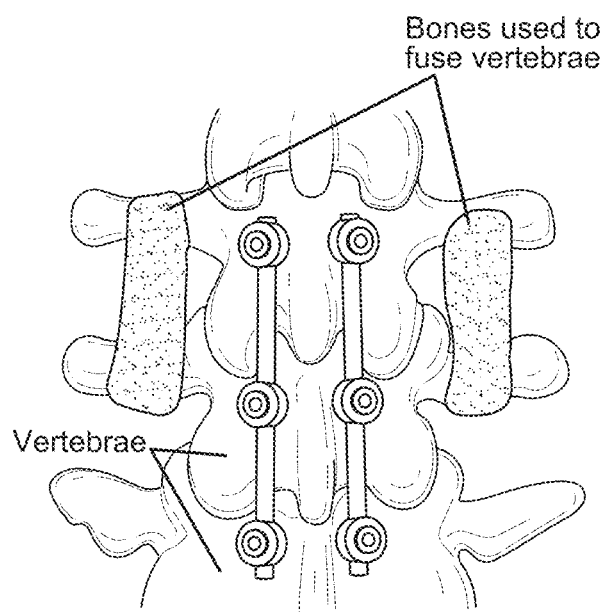
FIGS. 9A and 9B illustrate the use of bone tissue (with or without bone morphogenic protein) to fuse vertebrae.
Figure 9B:
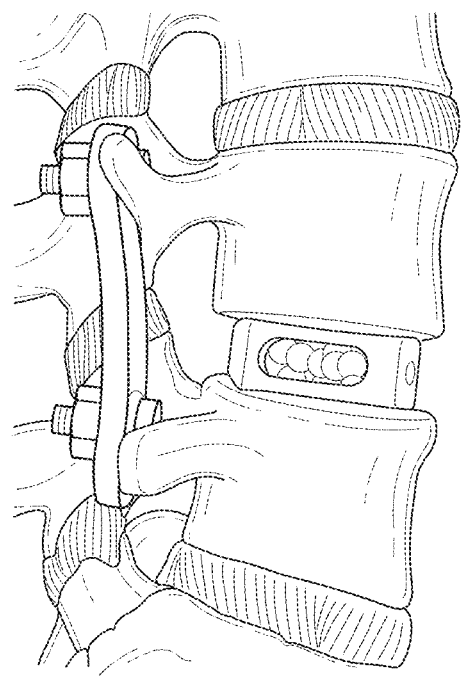

In order to address problems associated with intervertebral disc injuries or disease, spinal fusion surgery is often indicated. In this surgery, two or more adjacent vertebrae (vertebral bodies) are fused together by creating a 'bony bridge' across the damaged/diseased intervertebral disc, for example, by using autologous or allograph bone tissue (as shown in FIGS. 9A and 9B). FIG. 9A illustrates a Posterolateral spinal fusion (bony fusion occurs between the transverse processes of the vertebrae) while FIG. 9B depicts an interbody spinal fusion (the bone graft is created between the bodies of the vertebrae in the area usually occupied by the intervertebral disc; the disc is often removed entirely and is typically replaced by a plastic or titanium cage to maintain alignment and height and promote bone growth). Fusion may also be augmented by fixation devices, including metal screws (including pedicle screws and a rod as shown in FIG.

Figure 8:
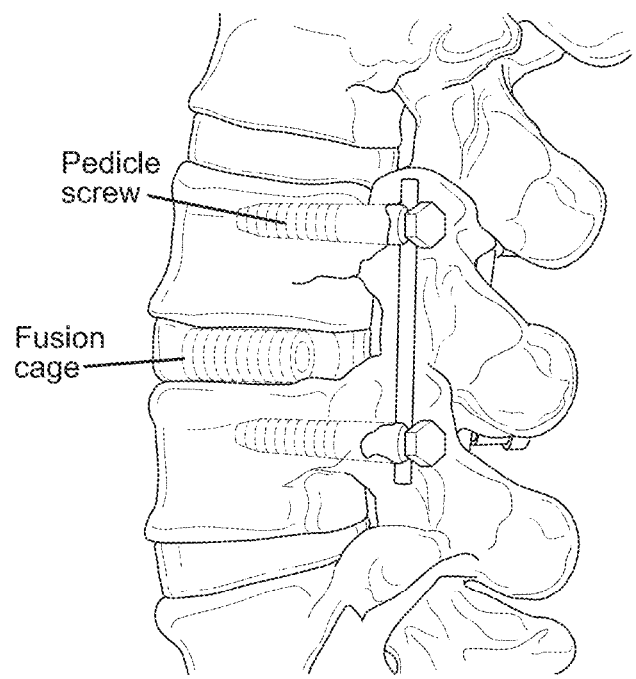
FIG. 8 illustrates spinal fusion surgery (spondylodesis or spondylosyndesis) demonstrating two embodiments wherein a pedicle screw (and supporting rod) are placed into the spine, as well as an interbody fusion cage.
Figure 10A:
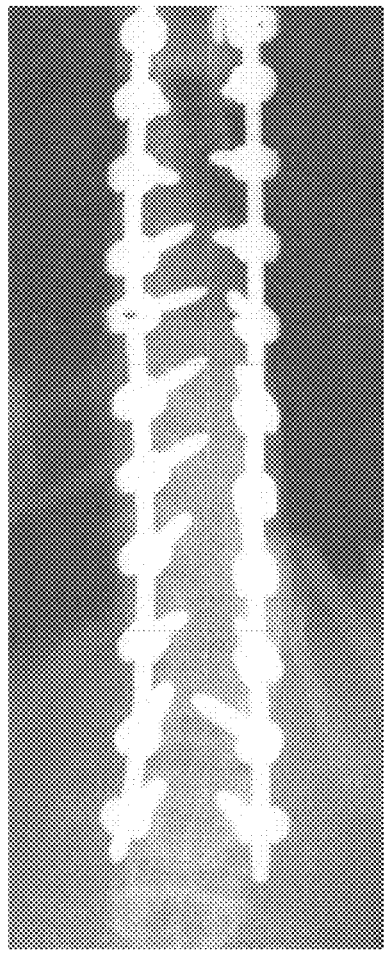
FIGS. 10A, 10B and 10C illustrate a variety of spinal fusion implants, including pedicle screws affixed to rods (FIGS. 10A and 10B), and a spinal plate retained by screws (FIG. 10C).
Figure 10B:
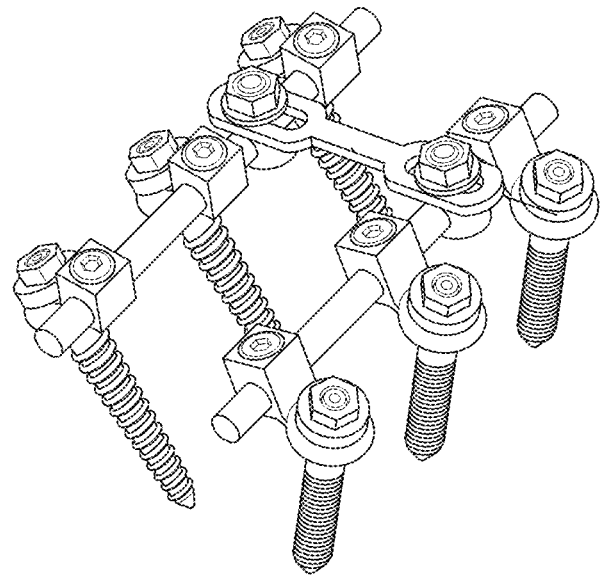
Figure 10C:
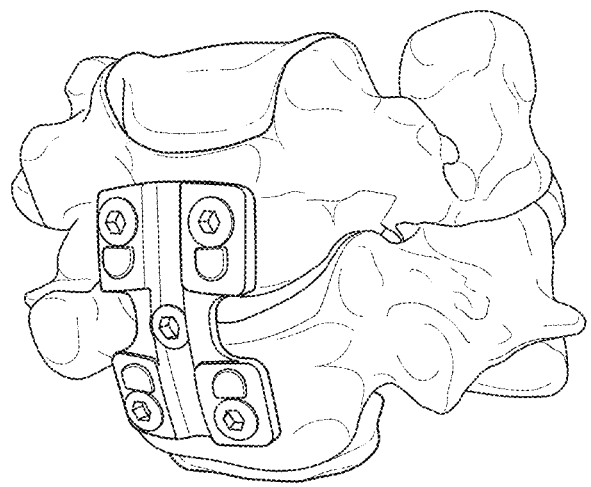

8), rods or plates to connect the screws, and fusion cages (including bone graft material which is placed inside a cage—an interbody fusion cage—see also FIG. 8 and FIG. 9B). FIG. 10 depicts a variety of spinal fusion devices, including pedicle screws affixed to rods (FIGS. 10A and 10B), as well as plates which can be utilized to fuse to vertebrae together (FIG. 10C).

Spinal fusion devices, and spinal fusion surgery in general can be associated with many complications, both during the surgery, as well as post-surgically. Typical complications include vertebral subluxation (abnormal movement between the vertebra), collapse of structural elements and loss of support, tissue-reaction against the device, infection, pseudo-arthritis, failure to heal properly (i.e., delayed union or non-union of the vertebrae) and problems with the implanted devices themselves such as: hardware fracture, loosening and/or migration; pedicle screw breakage, loosening or movement: and transitional syndrome (i.e., stress placed on nearby vertebrae due to the fusion).

Within various embodiments of the invention, sensors are described herein that can be placed on the spinal fusion devices, and/or instruments, in order to ensure that the devices are placed properly during surgery, and to monitor and assess their performance (or lack thereof) subsequent to surgery.

Figure 11A:
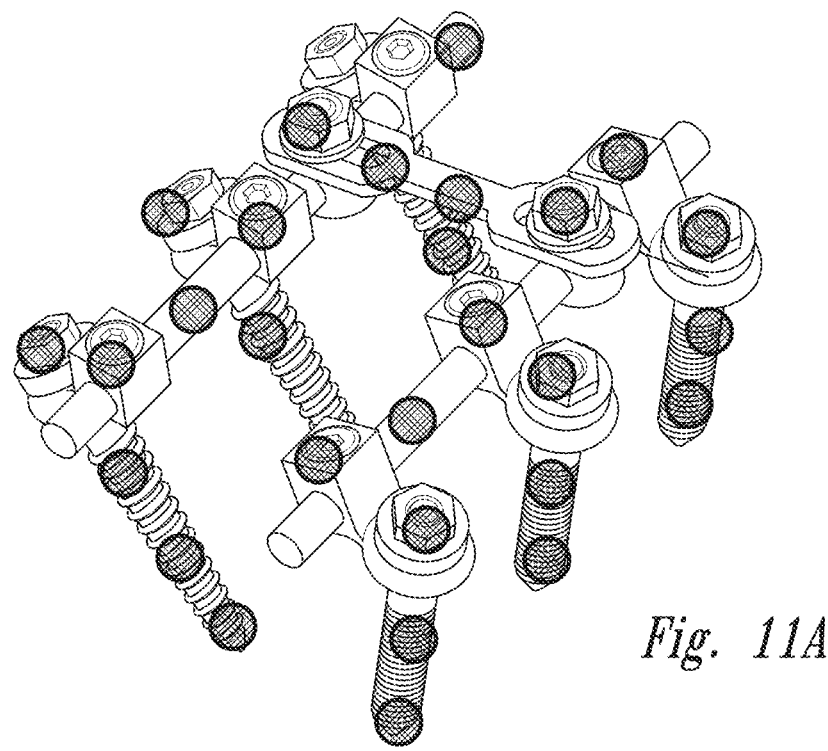
FIGS. 11A, 11B, 11C and 11D illustrate a variety of sensors on and/or within a spinal fusion implant (on or within pedicle screws and a rod).

For example, as shown in FIG. 11A, position sensors (shown as solid circles) can be provided on and/or within the pedicle screws, rods, wires and/or plates of a spinal fusion device. The position sensors can be utilized to assess the range of motion of the spinal segment (flexion and extension of the spinal segment, adduction and rotation of the spinal segment), to enhance the accuracy of physical exam (from 3D data which may be utilized to produce an image, and to assess position and movement of the spine and the device, to assess if there is subluxation between the segments), to monitor spinal and device anatomy (alignment, kyphosis), to assess the contact and interaction between adjacent device components (e.g., between screws, plates rods and/or wires), and to monitor for breakage, bending, loosening and/or movement of any of the implant parts. Collection of data from position sensors will also allow for both short-term and long-term assessment of product performance, as well as assessment of healing and patient recovery.

Figure 11B:
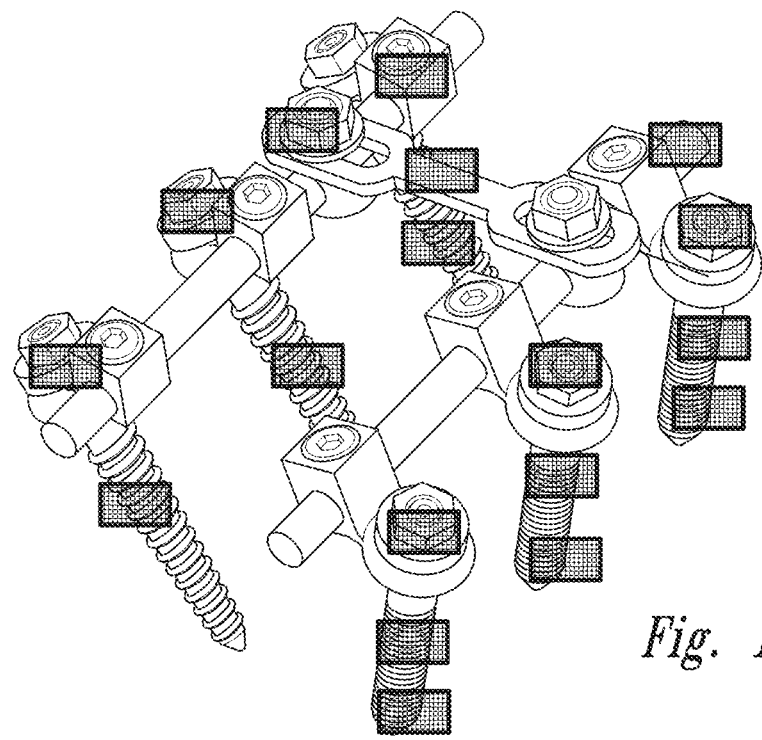

As shown in FIG. 11B, contact sensors (shown as rectangles) can also be placed on and/or within the pedicle screws, rods, wires and/or plates of a spinal fusion device. The contact sensors can be utilized to detect the space, movement and integrity of the bond between the hardware and the surrounding tissues, and the integrity of the connections between the various different pieces of hardware (disconnection of the hardware components), bending or breakage of the hardware pieces, and to detect loosening and/or osteolysis associated with the hardware (bone loss in the tissues surrounding the implanted devices; particularly for screws). Collection of data from contact sensors will also allow for both short-term and long-term assessment of product performance, as well as assessment of healing and patient recovery.

Figure 11C:
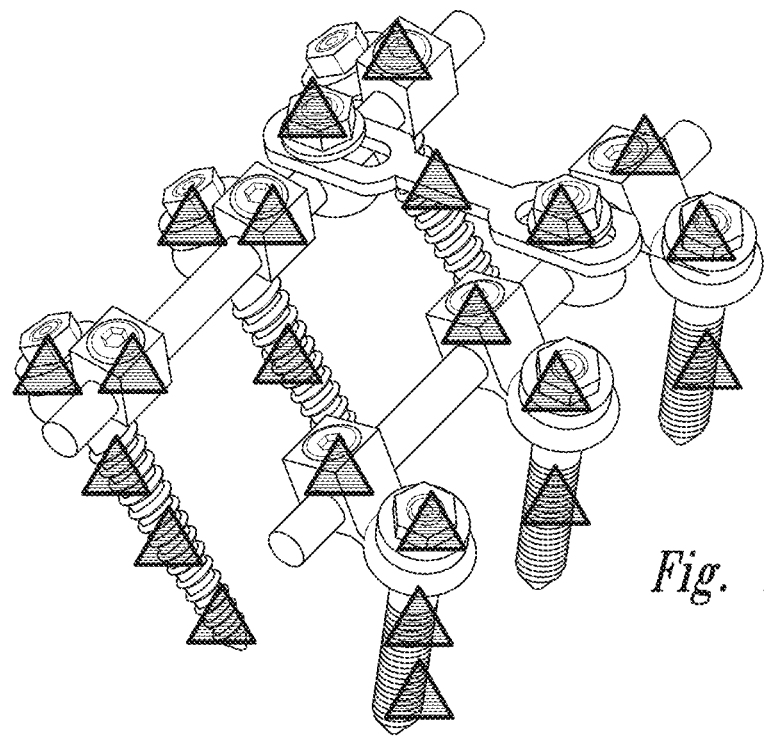

FIG. 11C depicts a variety of accelerometers and/or strain gauges (shown as triangles) which can be placed on and/or within the pedicle screws, rods, wires and/or plates of a spinal fusion device. The sensors can be utilized to indicate strains (and/or repetitive strains over time) that can result in destructive bone remodeling. In addition, the sensors can detect and record the magnitude, direction of acceleration, orientation, vibration and shock of a given strain. Hence, loosening of screw in bone, movement between components, vertebral subluxation (spondylolisthesis), breakage and/or failure of components, and the collapse of structural elements (including damage to the surrounding bone) can also be monitored and recorded. The data can also be integrated and utilized to create a 2D and/or 3D image of the hardware and spinal anatomy, both at a single point as well as over time based upon real-world stresses. Such sensors also allows for the continuous monitoring of the device in order to assess both short-term and long-term assessment of product performance, as well as assessment of healing and patient recovery.

Figure 11D:
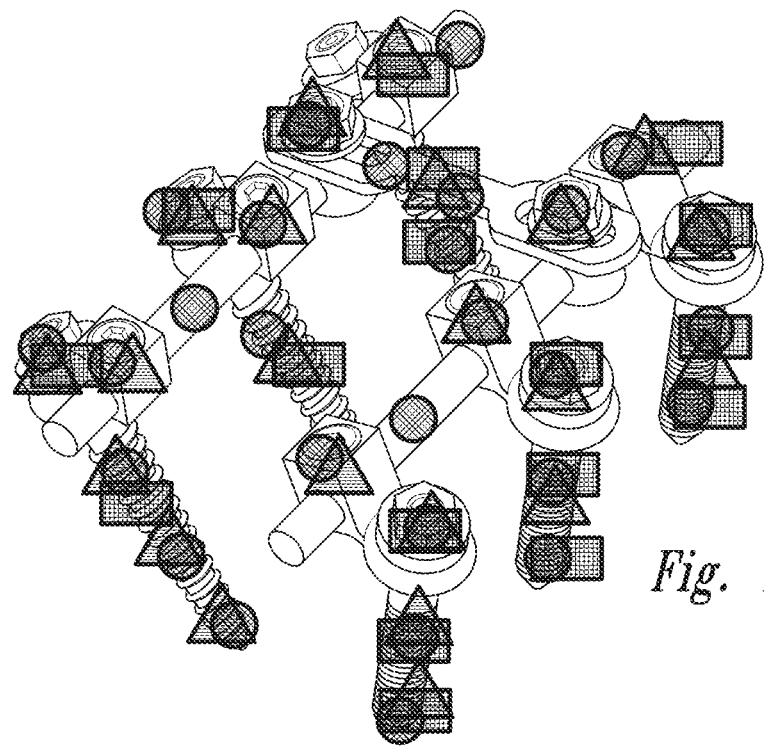

As shown in FIG. 11D, a wide variety of sensors may be placed on the spinal fusion devices (e.g., on or within the pedicle screws, wires, rods and/or plates), including for example, one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed on any or all of the spinal fusion devices (e.g., on or within the pedicle screws, wires, rods and/or plates) at a density of greater than 1, 2, 3, 4, 5, 6, 7, 8, 9, 10 or greater than 10 sensors per square centimeter. Within other aspects sensors are placed on the spinal fusion devices (e.g., on or within the pedicle screws, wires, rods and/or plates) at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

A3. Degenerative Disc Disease (DDD)/Interbody Fusion/Spinal Cages

Figure 1B:
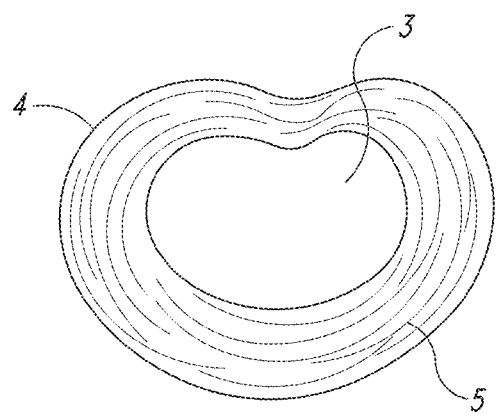
Figure 1C:
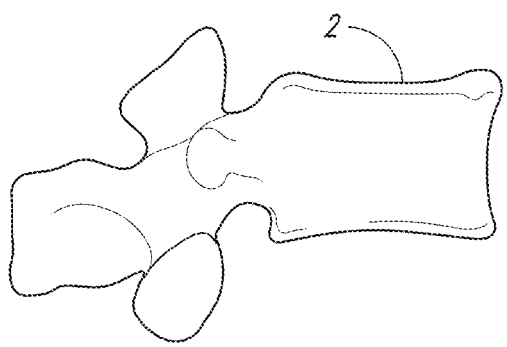
Figure 17A:
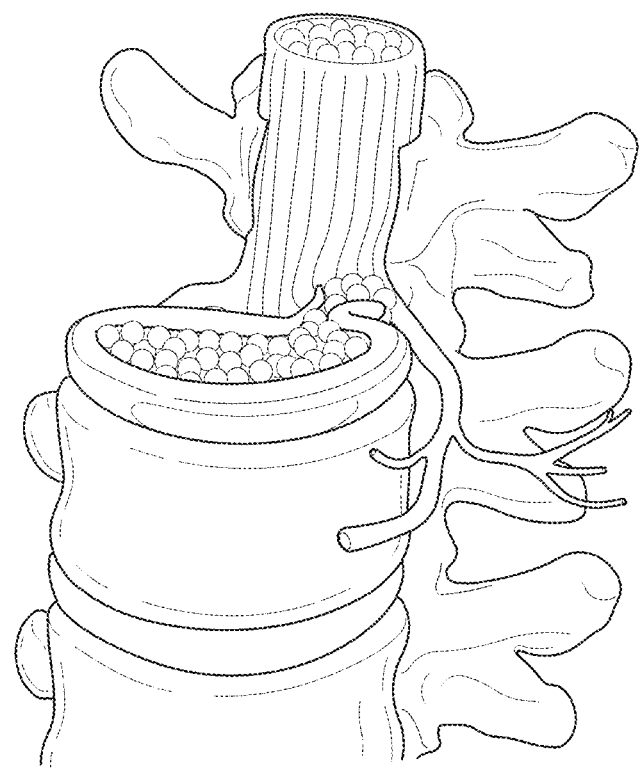
FIG. 17A and FIG. 17B illustrate two different views of a vertebral column with a herniated intervertebral disc applying pressure to the spinal cord and/or the spinal nerves.
Figure 17B:
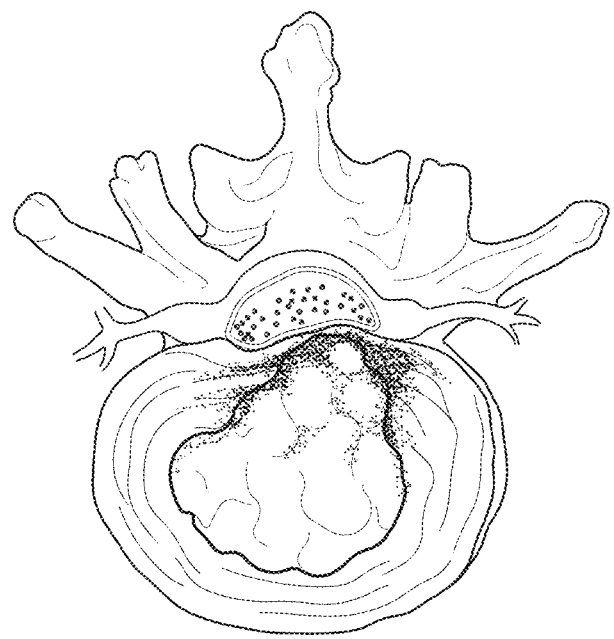

Degenerative Disc Disease, also known as spondylosis, is typically a disease associated with aging (although it can also be caused by injury or trauma), and can be associated with chronic neck and/or back pain and peripheral nervous symptoms (numbness, tingling, weakness, bowel and bladder problems). Fibrocartilage typically develops in the intervertebral disc as a result of aging or repeated injury. Contents of the nucleus pulposis (the inner, gelatinous part of the disc, Number 3 in FIG. 1B) can bulge or herniate (protrude, shown in FIGS. 17A&B) through weakened areas of the annulus fibrosis (the outer, stronger part of the disc, Number 5 in FIG. 1B) and come into contact with the spinal cord or the spinal nerves. It is the pressure from the bulging or herniated disc on the spinal cord (as shown in FIG. 17B) or the spinal nerves (as shown in FIG. 17A) that leads to the pain and neurological symptoms described previously.

Spinal cages have been developed in order to assist with interbody fusion, and can be utilized to treat Degenerative Disc Disease, herniated discs, and low grade spondylolisthesis. They are typically small, hollow cylindrical devices composed of titanium, titanium alloys, stainless steel, or polymers. They can be filled with bone graft material (allograft or autograft) and/or growth factors (e.g. bone morphogenic protein, BMP)

Figure 12A:
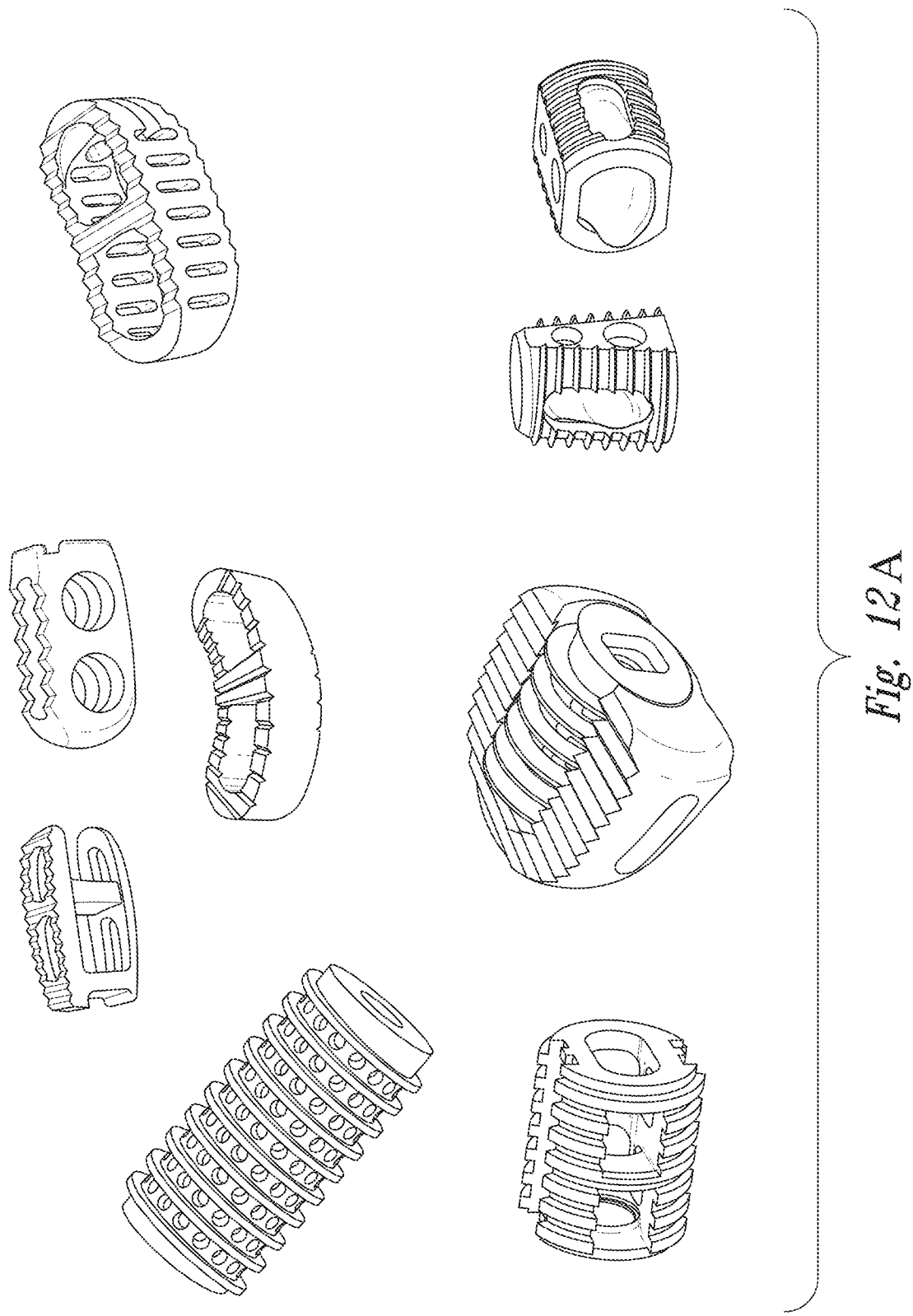
FIGS. 12A, 12B and 12C illustrate a variety of spinal (interbody) cages some of which are hollow to allow the incorporation of bone graft material.
Figure 12B:
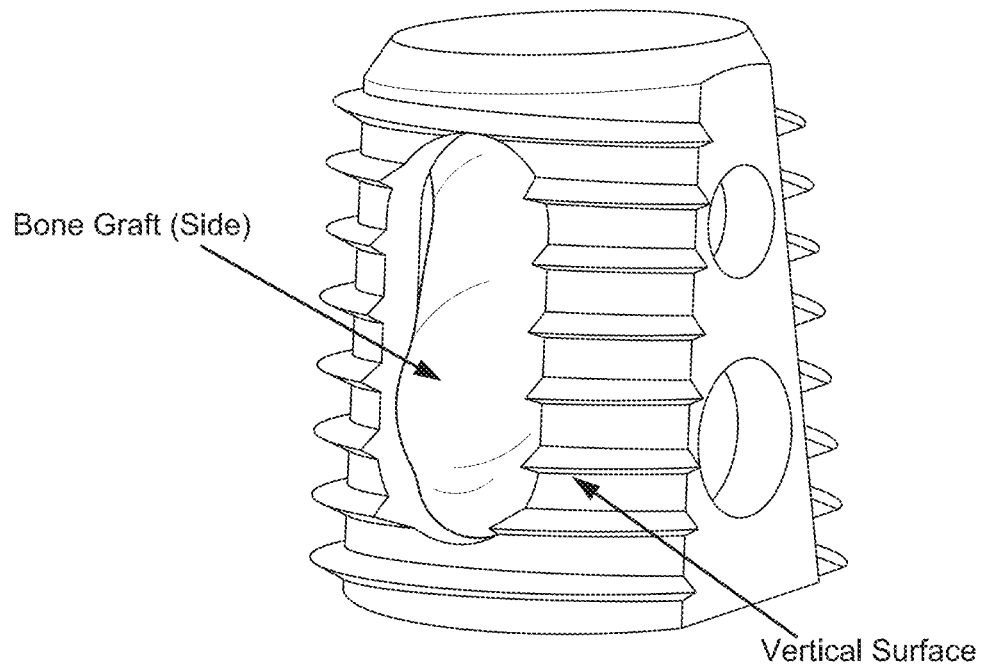
Figure 12C:
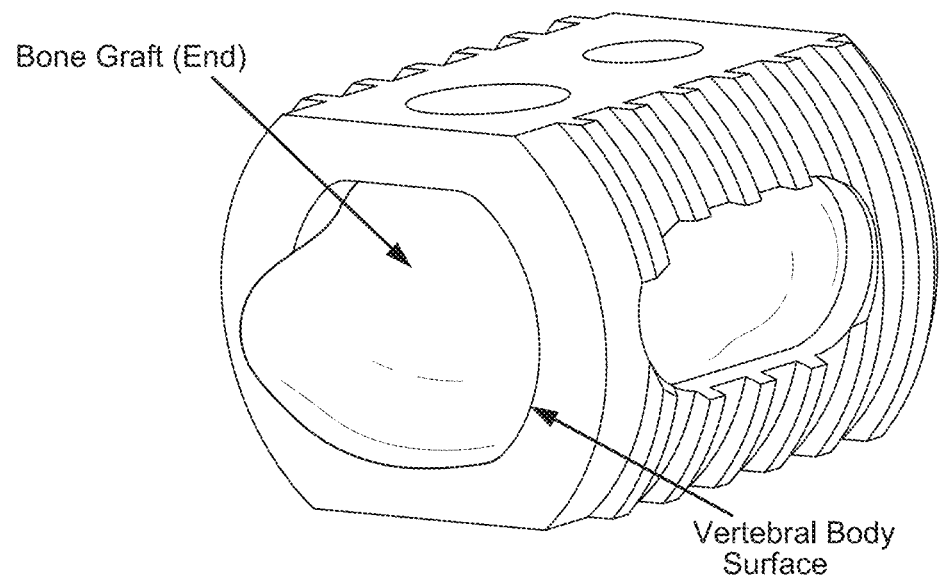

As shown in FIG. 12A, a wide variety of spinal cages are presently available commercially from a number of manufacturers (e.g., BAK from Sulzer Spine Tech, Ray TFC from Stryker, Contact Fusion Cage from Synthes, and Interfix Cage and LT Cage from Medtronic). Spinal cages can be manufactured to be placed between the vertebral bodies of the spine in a particular orientation. For example, as shown in FIGS. 12B and 12C, spinal cages may have a specific orientation (e.g., a vertebral body side and a vertical side). Furthermore, the vertical sides can be flattened to allow the placement of two cages side-by-side in the intervertebral space. The spinal cage can be packed during surgery with autologous or allogeneic bone graft material, with or without other factors such as bone morphogenic proteins ("BMPs"), in order to assist in bone growth through the perforated walls of the cage, and the formation of a bony fusion between the vertebrae.

Figure 13A:
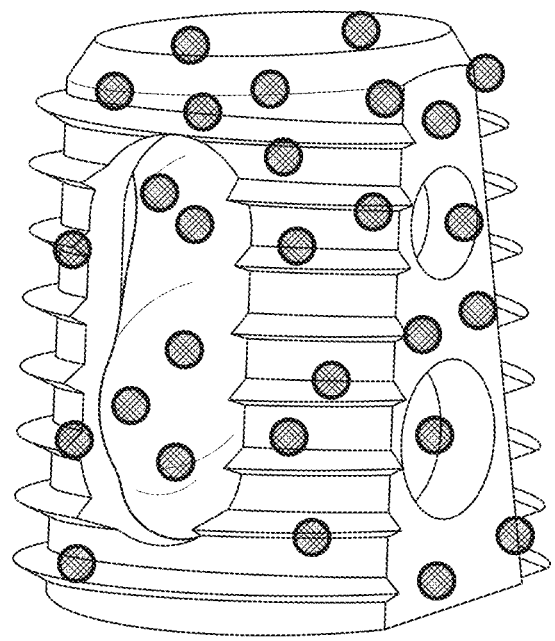
FIGS. 13A, 13B, 13C and 13D illustrate spinal (interbody) cages having a variety of sensors and associated bone graft material having a variety sensors.
Figure 13B:
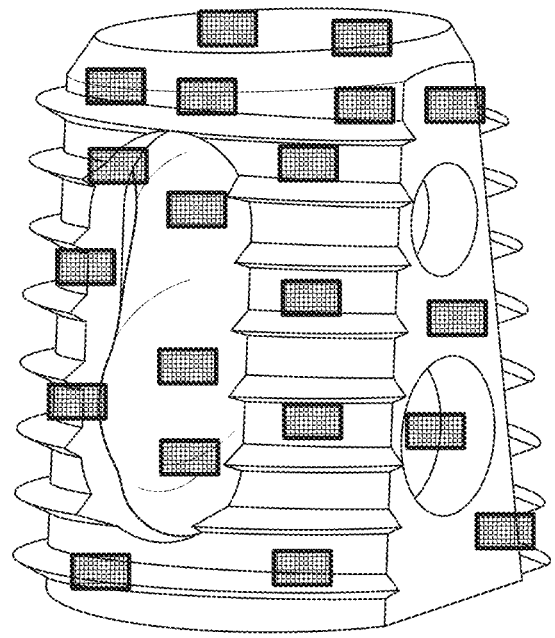

Within various embodiments of the invention position sensors can be placed on and/or within a spinal cage. For example, as illustrated in FIG. 13A, position sensors (shown as solid circles) can be placed on and/or within the bone graft material, and/or on and/or within the spinal cage. The sensors can be utilized to detect and monitor location and fixation of the affected spinal cage, movement of the cage within the intervertebral space, to monitor breakage and/or wear of the spinal cage, and to monitor the anatomy, contact and interaction between adjacent components (particularly when more than one cage is used). For example, during placement, the position sensors can be utilized to determine if the cages are correctly placed, if spinal alignment is correct, and if intervertebral spacing is optimal; following placement, the position sensors can monitor any movement, migration, or breakage of the spinal cage; furthermore, they can be used to follow the progress of bony fusion as spinal cage movement should become progressively less as new bone growth successfully fuses the two segments together (and "locks" the cages within the bone mass); conversely, ongoing positional movement or increasing positional movement would be cause for concern that fusion is not progressing as expected. Positional sensors therefore allow for the continuous monitoring of the device, spinal anatomy (alignment, spacing, etc.) and bony fusion in order to assess both short-term and long-term product performance, as well as assessment of healing and patient recovery.

Similarly, as illustrated in FIG. 13 B contact and pressure sensors (shown as rectangles) can be placed on and/or within the bone graft material and/or within the spinal cage. Within certain embodiments of the invention two cages are provided with "matching" sensor placement, in order to allow an analysis of movement and/or migration between the different (paired) pieces of spinal cage hardware. Contact sensors can also be utilized to detect space, movement, and the integrity of bond between the hardware and the developing bony tissue. For example, increasing contact and/or decreasing pressure between the hardware and the surrounding tissue is suggestive of ongoing fusion (i.e. the new bone growth is assuming the compressive forces and decreasing the dependence on the cage), while eventual contact/pressure stabilization suggests healing is almost complete; such measurements can guide rehabilitation and physiotherapy decisions. On the other hand, lessening of contact between the bone tissue and the cage might suggest inadequate bone growth, failure of fusion, or failure of the device; increasing pressure on the cage in this context would suggest that the device (and not the new bone growth) is taking a disproportionate amount of the compressive forces between the intervertebral bodies. The sensors also allow for the continuous monitoring of the device in order to assess both short-term and long-term product performance, as well as assessment of healing and patient recovery and can help guide activity and recovery regiments.

Figure 13C:
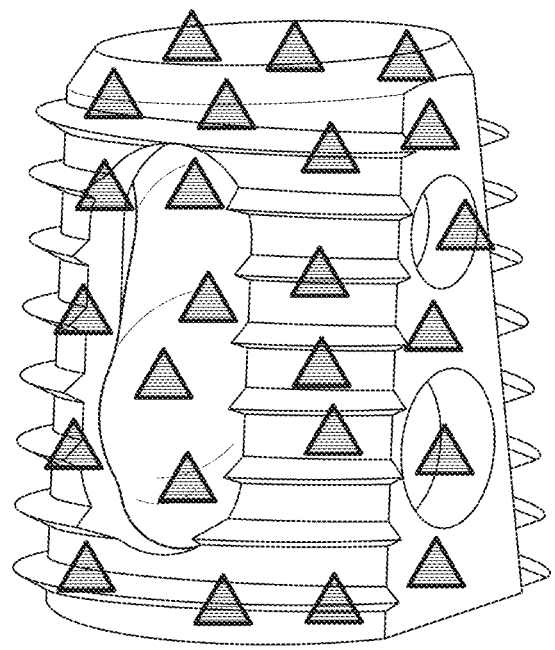

FIG. 13C depicts a variety of accelerometers and/or strain gauges (shown as triangles) which can be placed on and/or within the bone graft material and/or on and/or within the spinal cage. The sensors can be utilized to detect and record the magnitude, direction of acceleration, orientation, vibration and shock of a given strain. Hence, detection of vibration/movement may indicate loosening within the fused disc, movement between paired spinal cage components (if more than one cage is used), breakage/failure of the spinal cage, migration of the cage(s), vertebral subluxation (spondylolisthesis), collapse of structural elements and loss of support, as well as damage to surrounding new bone. Data which is generated from the sensors can also be integrated and utilized to create a 2D and/or 3D image of the hardware and spinal anatomy, both at a single point, as well as over time, based upon real-world stresses. Accelerometers can provide the clinician with an understanding of the overall movement and stability of the affected spinal segment—the flexion, extension and rotation of the spinal segment (which if bony fusion is successful, should all decrease with time). Such sensors also allow for the continuous monitoring of the implanted device in order to monitor both short-term and long-term product performance, as well as assessment of healing and patient recovery. This data is helpful in monitoring patient progress and the effects of specific rehabilitation efforts as well as identifying potential activities/actions that are detrimental to recovery.

Figure 13D:
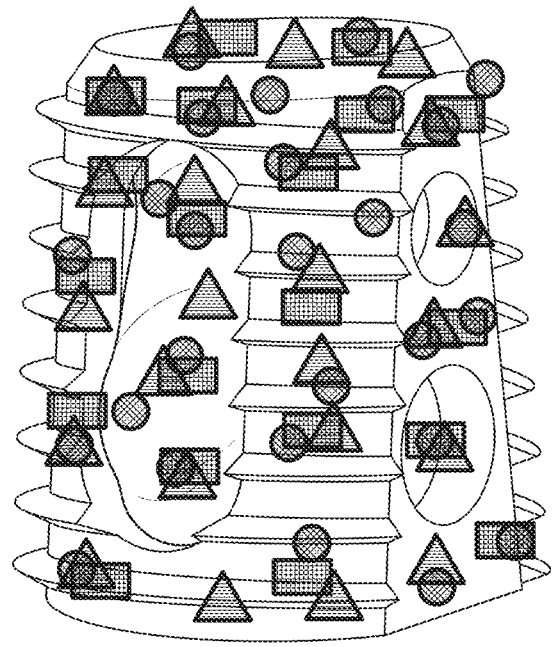

As shown in FIG. 13D, a wide variety of sensors may be placed on and/or within the bone graft material and/or on/within the spinal cage, including for example, one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed on any or all of the spinal fusion devices (e.g., on or within the spinal cages, the bone graft material and any other hardware utilized to complete the fixation such as pedicle screws, wires, rods and/or plates) at a density of greater than 1, 2, 3, 4, 5, 6, 7, 8, 9, 10 or greater than 10 sensors per square centimeter. Within other aspects sensors are placed on and/or within the bone graft material and/or on/within the spinal cage (and any other hardware utilized in the fusion such as pedicle screws, wires, rods and/or plates) at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

A4. Artificial Discs

Figure 15:
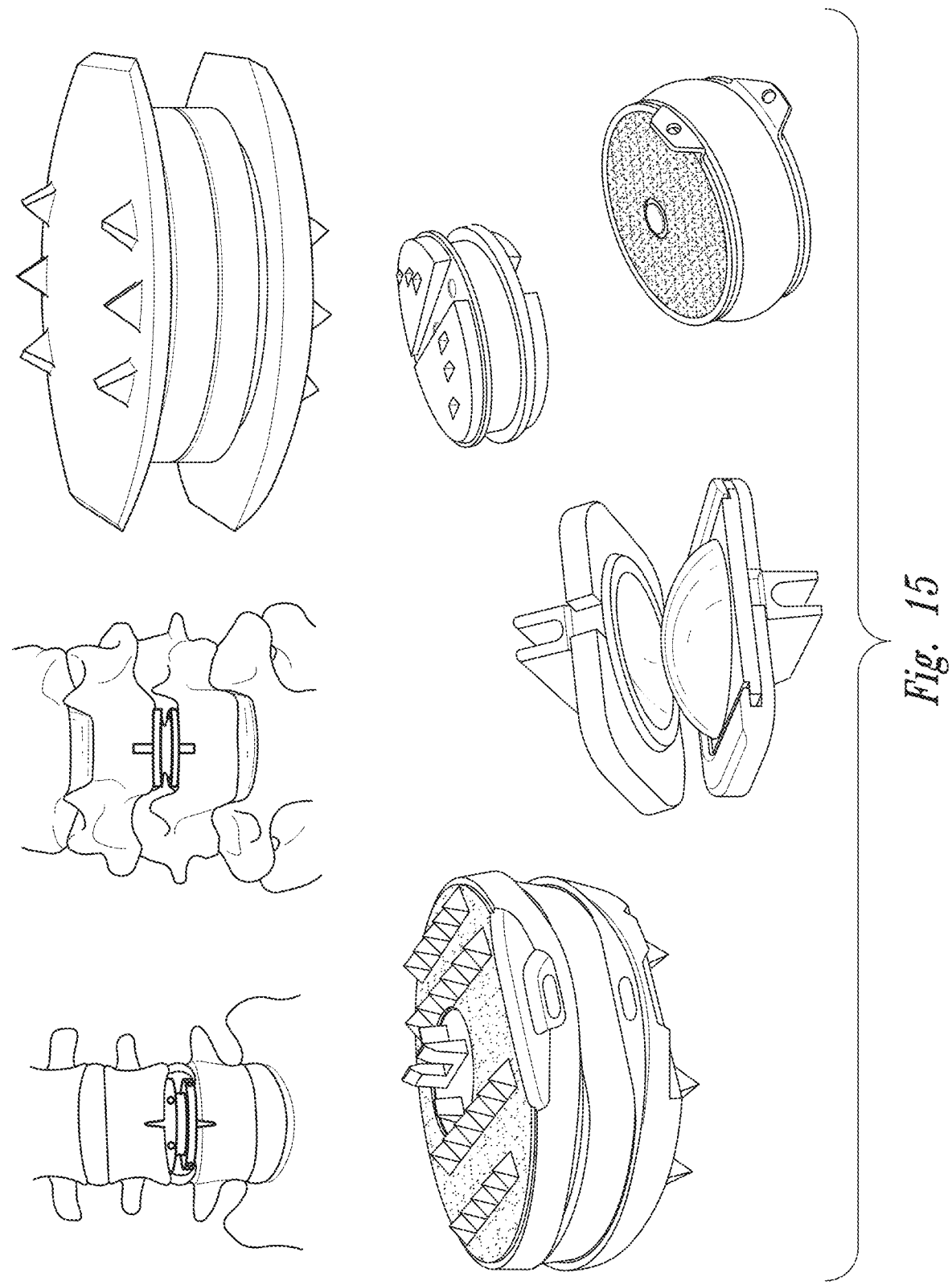
FIG. 15 illustrates a variety of artificial intervertebral discs.

Within various aspects of the present invention, intervertebral disc damage (e.g., injury or disease such as Degenerative Disc Disease) may also be treated utilizing artificial discs (i.e., by complete replacement of the damaged disc with a prosthetic replacement). The intent of an artificial disc is, unlike a spinal fusion, to preserve motion between the vertebrae, e.g., to provide for more natural spinal flexion, extension and rotation. Representative artificial discs are shown in FIG. 15, and include the Charite Lumbar Disc (DePuy), Prodisc Lumbar Disc (Synthes), ProDisc Cervical Disc (Synthes) and the Maverick Lumbar Dis (Medtronic).

Figure 14A:
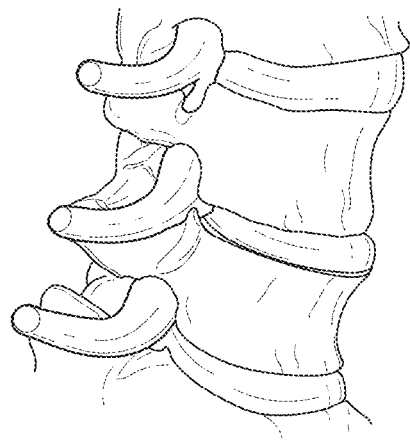
FIGS. 14A, 14B, 14C and 14D illustrate a surgical procedure wherein a diseased intervertebral disc is removed and an artificial disc is inserted into a subject.
Figure 14B:
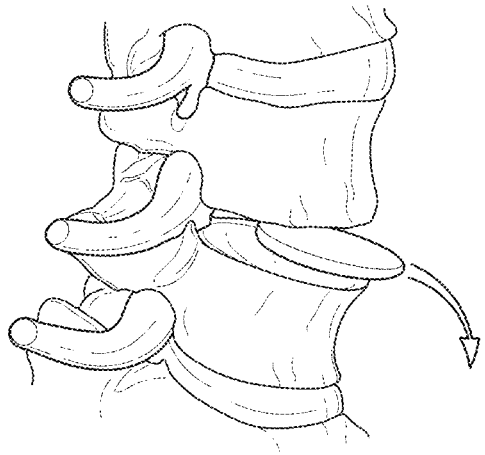
Figure 14C:
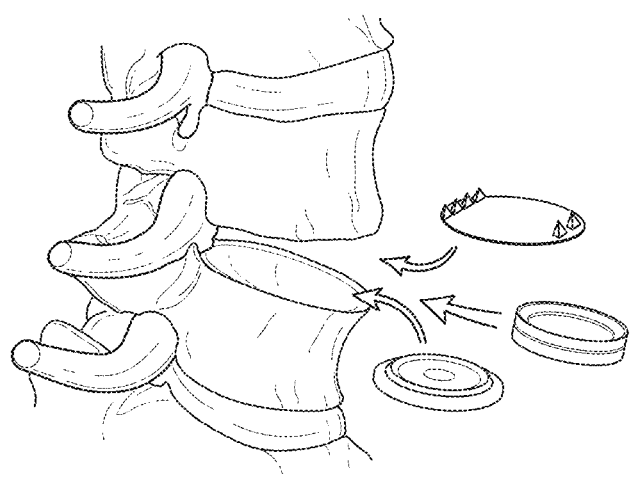
Figure 14D:
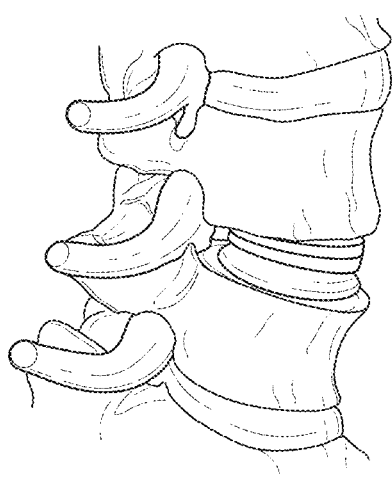

Typically, the intervertebral disc (FIG. 14A) is completely excised (FIG. 14B) by the surgeon via an anterior (abdominal) approach, and plates (usually composed of titanium or titanium alloys—FIG. 14C) are placed over the vertebral bodies. A core piece (usually comprised of a polymer such as polyethylene) is sized to provide the correct height and positioned between the plates (also FIG. 14C). The completed artificial disc is shown in FIG. 14D.

Figure 16A:
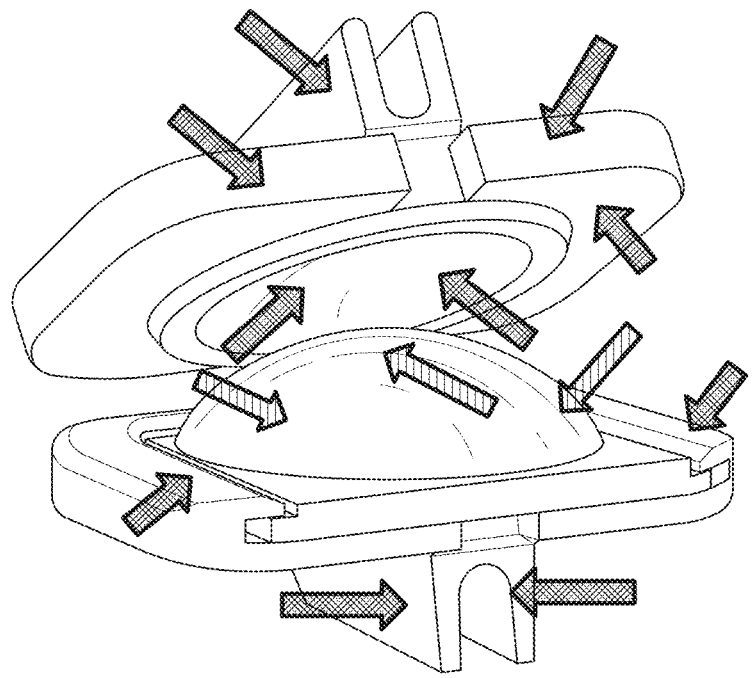
FIGS. 16A, 16B, 16C and 16D illustrate a variety of sensors on and in an artificial intervertebral disc.
Figure 16B:
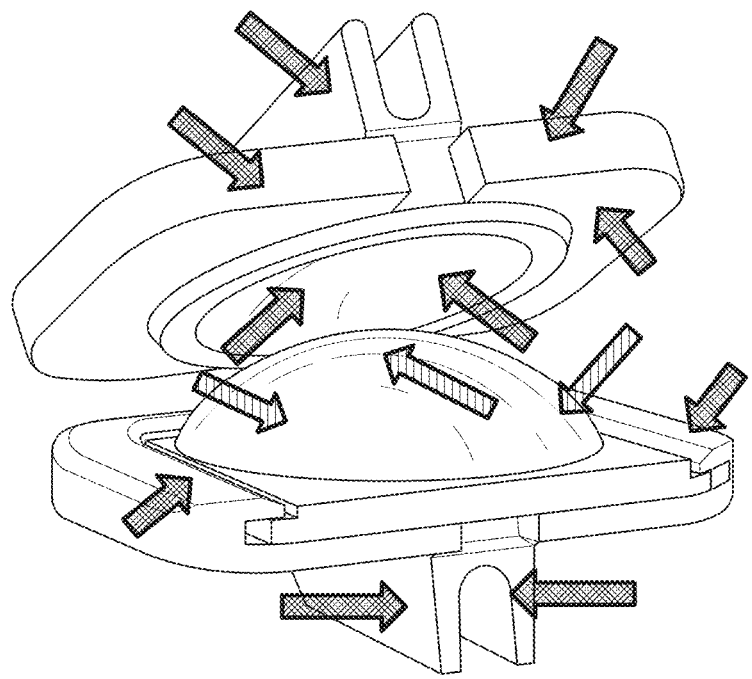

Within various embodiments of the invention, position sensors can be placed on and/or within an artificial disc. For example, as illustrated in FIG. 16A, position sensors can be placed on and/or within the artificial disc (i.e., on or within the metallic plates as shown by the black arrows, and/or on/within the articular core piece between the plates as shown by the lined arrows; for cemented prostheses, the position sensors can also be contained within the bone cement). Intraoperatively, the position sensors can be utilized by the surgeon to determine accurate placement, alignment and spinal anatomy (medical imaging). Postoperatively, the sensors can be utilized to detect and accurately monitor flexion, extension and rotation of the artificial disc (precise, numeric measurements of all motion), and to assess, measure and evaluate the range of motion of the spinal segment. The sensors can also be utilized to determine and monitor the location and fixation of the artificial disc, movement of the artificial disc, to monitor the anatomy, contact and interaction between adjacent components (detect normal component movement and abnormal component movement such as artificial joint dislocation or subluxation), and to monitor migration, breakage and/or wear of the artificial disc. It also allows for the continuous monitoring of the device in order to assess both short-term and long-term product performance, as well as assessment of healing and patient recovery.

Similarly, as illustrated in FIG. 16 B contact sensors can be placed on and/or within the artificial disc (i.e., on or within the metallic plates as shown by solid black arrows, and/or on/within the articular core piece between the plates as shown by the lined arrows; for cemented prostheses, the sensors can be contained within the bone cement). Intraoperatively, the contact sensors can be utilized by the surgeon to determine accurate placement, alignment and contact between the metallic plates and the surrounding tissues and between the components of the artificial disc (the metallic plates and the articular core). Postoperatively, contact sensors can also be utilized to detect space, movement, and the integrity of bond between the disc hardware (the metallic plates) and bone, and to detect increasing movement (which could be suggestive of osteolysis); to monitor articular surface contact (to identify artificial joint dislocation or subluxation); and to detect and/or monitor wear, erosion, migration and/or failure or breakage of the device. As demonstrated by FIG. 16D, contact sensors can also be contained at various depths within the polymeric articular core (as shown by the lined arrows) and within the metallic endplates (as shown by the solid arrows) to provide ongoing assessment of the amount of surface wear of the synthetic articular components. The sensors also allow for the continuous monitoring of the device in order to assess both short-term and long-term product performance, as well as assessment of healing and patient recovery.

Figure 16C:
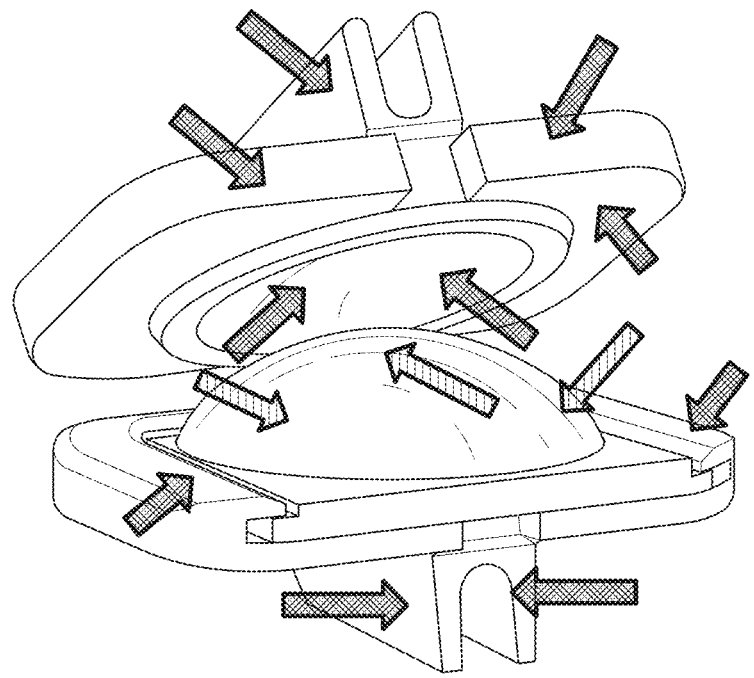

FIG. 16C depicts a variety of accelerometers and/or strain gauges which can also be placed on and/or within the artificial disc (e.g., on or within the metallic plates as shown by the solid black arrows, and/or on/within the articular core piece between the plates as shown by the lined arrows; for cemented prostheses, the sensors can be contained within the bone cement). The sensors can be utilized to detect and record the magnitude, direction of acceleration, orientation, vibration and shock of a given strain. Hence, detection of vibration/movement may indicate loosening of the prosthetic disc from the surrounding bone (improper fixation or osteolysis); or within the artificial disc, vibration/movement may be an indicator of migration/breakage/failure of the artificial disc, vertebral artificial joint subluxation or dislocation, collapse of the structural elements and loss of support, as well as damage to surrounding new bone. Data which is generated from the sensors can also be integrated and utilized to create a 2D and/or 3D image of the hardware and spinal anatomy, both at a single point as well as over time based upon real-world stresses. Accelerometers can provide the clinician with an understanding of the overall movement and stability of the affected spinal segment—the flexion, extension and rotation of the spinal segment containing the artificial disc. Such sensors also allow for the continuous monitoring of the device under "real world" conditions in order to assess both short-term and long-term performance, as well as assessment of healing and patient recovery. This data is helpful in monitoring patient progress and the effects of specific rehabilitation efforts as well as identifying potential activities/actions that are detrimental to recovery.

Figure 16D:
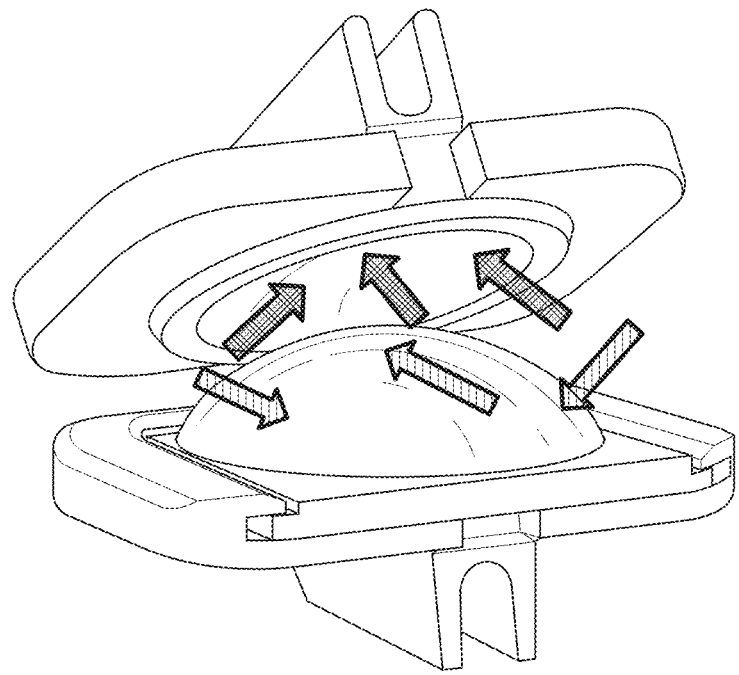

As shown in FIG. 16D, a wide variety of sensors may be placed on and/or within the artificial disc in order to detect and monitor articular surface wear in the metal plates and/or polymer components (if present). Within various embodiments contact and/or pressure sensors may be layered at various depths within the metallic plate (the solid black arrows in FIG. 16D) or within the polymeric articular surface (the lined arrows in FIG. 16D). The sensors may then be uncovered (and activated) as the surface above them is worn away or damaged, indicating the extent and depth of surface loss, and providing a diagnostic to determine the relevant remaining effective lifespan of the implant.

In summary, a wide variety of sensors may be placed on and/or within the artificial disc (i.e., on or within the metallic plates, and/or on/within the articular core piece between the plates; for cemented prostheses, the sensors can also be contained within the bone cement) in order to provide an evaluation of performance in the clinic as well as 'real-world' settings, to detect loosening between the prosthesis and the surrounding bone, to detect joint subluxation or dislocation, to monitor spinal anatomy and alignment, to detect infection and/or inflammation, to detect the strain encountered in the prosthesis, to detect acceleration and impact events, and to detect articular surface wear in the metal plates and/or polymer components (if present). For example, the artificial disc can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed on any or all of the artificial disc devices (e.g., on or within the metallic plates, and/or on/within the articular core piece between the plates; for cemented prostheses, the sensors can be contained within the bone cement) at a density of greater than 1, 2, 3, 4, 5, 6, 7, 8, 9, 10 or greater than 10 sensors per square centimeter. Within other aspects sensors are placed on and/or within the artificial disc (e.g., on or within the metallic plates, and/or on/within the articular core piece between the plates; for cemented prostheses, the sensors can be contained within the bone cement) at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

A5. Microdiscectomy

Within various aspects of the present invention, devices and methods are provided for treating herniated discs. Briefly, unlike a typical vertebrae (FIG. 17A), a tear in the Annulus Fibrosis of the disc allows the soft, central Nucleus Pulposis to herniate out through the Annulus. This may occur for a variety of reasons, e.g., trauma, lifting, repeated injury, or may be idiopathic in nature. Such herniated discs may be initially treated conservatively with rest, anti-inflammatory medication, and physiotherapy, but in certain cases, surgery may be required if the nerve roots or spinal cord are involved (see, e.g., FIG. 17A, wherein the disc is herniated, resulting in compression of the nerve roots and FIG. 17B where the disc is herniated resulted in compression of the spinal cord) and neurological symptoms (numbness, weakness, tingling, paralysis, bowel or bladder dysfunction) are present.

In a typical surgical procedure, a patient is anesthetized, and a small incision is made in the back. The spinal muscles and ligaments are separated, and a small amount of the facet joint may be removed. The herniated disc material is then removed endoscopically (see FIG. 18).

Within various embodiments, microdiscectomy tools containing sensors, as described herein, are provided. For example, within one embodiment microdiscectomy tools containing contact sensors are provided which can be utilized to monitor contact between the rongeur and nerve root, spinal cord and/or surrounding nerve tissue. Microdiscectomy tools containing pressure sensors may be utilized to monitor pressure exerted on the nerve tissue during dissection, and to prevent tissue damage and nerve injury from excessive pressure. Microdiscectomy tools containing position sensors and accelerometers can be utilized to assist in resection of herniated disc tissue, and used for medical imaging (e.g., to provide an image of spinal and disc anatomy, the herniated segment, and disc wall) pre and post-resection. Within certain embodiments of the invention, a naturally occurring or synthetic nucleus-like material may be reinjected back into the disc (see generally, Eur Spine J. 2009 November; 18(11): 1706-1712. Published online 2009 Aug. 18). Within preferred embodiments, the naturally occurring or synthetic nucleus-like material may contain one or more sensors to monitor pressure, position, contact and/or movement within the nucleus, as well as leaks or ruptures of the disc and inflammation and/or infection of the disc.

Within other aspects of the invention Intradiscal Electrothermal Annuloplasty can be utilized to treat, for example, Degenerative Disc Disease. For example, as shown in FIG. 19A, an electrothermal catheter can be inserted along the back inner wall of the disc. The catheter is then heated as shown in FIG. 19B, thereby thickening collagen fibers which make up the disc wall (and sealing any ruptures in the disc wall), and cauterizing sensitive nerve endings.

Within various embodiments of the invention electrothermal catheters are provided comprising one or more sensors that can be utilized in the process of Intradiscal Electrothermal Annuloplasty. For example, contact sensors can be utilized to monitor contact between the electrothermal catheter and the inner wall of the annulus. Pressure sensors can be utilized to monitor the pressure in the annulus, to aid in avoiding perforation through the annulus, and to confirm the integrity/sealing of the annulus post-procedure. Position sensors and accelerometers can be utilized to assist in catheter placement, and used for medical imaging (e.g., to confirm correct catheter placement and to image spinal anatomy and disc anatomy, both pre and post-treatment). In addition, temperature sensors can be utilized to control the heat of the catheter, in order to ascertain and maintain the correct operating temperature (and prevent thermal injury to non-target tissues).

In summary, a wide variety of sensors may be placed on and/or within microdiscectomy and electrothermal catheter tools in order to provide "real time" information and feedback to the surgeon during the procedure, to detect instrument placement, spinal and disc anatomy, forces exerted on surrounding tissues, and to detect the strain encountered in an interventional procedure. For example, the microdiscectomy and electrothermal tools can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

A6. Bone Cement and Other Implantable Materials

As described herein bone cement is utilized in a large number of spinal procedures. Most typically, methylmethacrylates are utilized (e.g., polymethylmethacrylate, or amethylmethacrylate—styrene copolymer), although other materials can also be utilized.

However, a wide variety of implantable materials can also be utilized (see generally US 2007/0100449). For example, suitable materials include both biocompatible polymers, therapeutic agents, and naturally occurring materials. Biocompatible polymers may be both bioabsorbable and/or nonbioabsorbable. Typically, the polymers will be synthetics (e.g., aliphatic polyesters, poly(amino acids), copoly(etheresters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), copolymers of lactide (e.g., D,L lactide), glycolides, caprolactones and blends and copolymers thereof. However, in certain embodiments natural polymers can also be utilized (e.g., fibrin-based materials, collagen-based materials, hyaluronic acid-based materials, glycoprotein-based materials, cellulose-based materials, silks and combinations thereof).

Within certain embodiments of the invention the bone cement or implantable material may contain a desired agent, compound, or matrix, such as, for example, bone morphogenic protein or "BMP", bone graft material, and calcium phosphate.

The bone cement and other implantable materials described herein may contain one or more sensors, including for example, fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the bone cement or implantable material will sensors at a density of greater than 1, 2, 3, 4, 5, 6, 7, 8, 9, 10 or 20 sensors per square centimeter; and or sensors a density of greater than 1, 2, 3, 4, 5, 6, 7, 8, 9, 10 or 20 sensors per cubic centimeter A7. Manufacturing Methods Within various embodiments of the invention, methods are also provided for manufacturing a spinal implant or device, medical delivery device for a spinal implant or device, or further compositions (e.g., fillers) having one of the sensors provided herein. For example, within one embodiment of the invention sensors can be placed directly into, onto or within: 1) spinal devices or implants (e.g., pedicle screws, spinal rods, spinal wires, spinal plates, spinal cages, artificial discs, bone cement, growth factors (Bone Morphogenic Protein BMP) as well as combinations of these (e.g., one or more pedicle screws and spinal rods, one or more pedicle screws and a spinal plate); and/or 2) medical delivery devices for the placement of spinal devices and implants (e.g., kyphoplasty balloons, catheters (including thermal catheters and bone tunnel catheters), bone cement injection devices, microdiscectomy tools and other surgical tools; and/or 3) further components or compositions (e.g., fillers such as bone cement (PMMA), growth factors (such as BMP) and/or other polymers) at the time of manufacture, and subsequently sterilized in a manner suitable for use in subjects.

Within further embodiments, the present disclosure provides a method of making a spinal implant or device, medical delivery device for a spinal implant or device, or further compositions (e.g., fillers) by 3D printing, additive manufacturing, or a similar process whereby the spinal implant or device, medical delivery device for a spinal implant or device, or further compositions (e.g., fillers) is formed from powder or filament that is converted to a fluid form that subsequently solidifies as the desired shape. For convenience, such processes will be referred to herein as printing processes or 3D printing processes. The present disclosure provide a method of making a spinal implant or device, medical delivery device for a spinal implant or device, or further compositions (e.g., fillers) by a printing process, where that spinal implant or device, medical delivery device for a spinal implant or device, or further compositions (e.g., fillers) includes a sensor, circuit or other feature as disclosed herein (collectively sensor or sensors). The sensor may be separately produced and then incorporated into the spinal implant or device, medical delivery device for a spinal implant or device, or further compositions (e.g., fillers) during the printing process. For example, a sensor may be placed into a desired position and the printing process is carried out around the sensor so that the sensor becomes embedded in the printed spinal implant or device, medical delivery device for a spinal implant or device, or further compositions (e.g., fillers). Alternatively, the printing process may be started and then at appropriate times, the process is paused to allow a sensor to be placed adjacent to the partially completed spinal implant or device, medical delivery device for a spinal implant or device, or further compositions (e.g., fillers). The printing process is then re-started and construction of the spinal implant or device, medical delivery device for a spinal implant or device, or further compositions (e.g., fillers) is completed. The software that directs the printing process may be programmed to pause at appropriate predetermined times to allow a sensor to be added to the partially printed spinal implant or device, medical delivery device for a spinal implant or device, or further compositions (e.g., fillers).

In addition, or alternatively, the sensor itself, or a portion thereof may be printed by the 3D printing process. Likewise, electronic connectively to, or from, or between, sensors may be printed by the 3D printing process. For example, conductive silver inks may be deposited during the printing process to thereby allow conductivity to, or from, or between sensors of a spinal implant or device, medical delivery device for a spinal implant or device, or further compositions (e.g., fillers). See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides spinal implant or device, medical delivery device for a spinal implant or device, or further compositions (e.g., fillers) wherein the sensor is printed onto a substrate, or a substrate is printed and a sensor is embedded or otherwise incorporated into or onto the substrate, or both the substrate and the sensor are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the spinal implant or device, medical delivery device for a spinal implant or device, or further compositions (e.g., fillers) is of a particularly intricate shape, it may be printed with two materials. The first material is cured (using, e.g., actinic radiation) as it is deposited, while the second material is uncured and can be washed away after the spinal implant or device, medical delivery device for a spinal implant or device, or further compositions (e.g., fillers)s has been finally printed. In this way, significant hollow spaces may be incorporated into the spinal implant or device, medical delivery device for a spinal implant or device, or further compositions (e.g., fillers).

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor may be embedded into the alloy powder bed, and the laser melts the powder around the sensor so as to incorporate the sensor into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating sensor-containing spinal implant or device, medical delivery device for a spinal implant or device, or further compositions (e.g., fillers), the method comprising forming at least one of a sensor and a support for the sensor using a 3D printing technique. Optionally, the 3D printing technique may be an additive manufacturing technique. In a related embodiment, the present disclosure provides a spinal implant or device, medical delivery device for a spinal implant or device, or further compositions (e.g., fillers) that is produced by a process comprising a 3D printing process, such as an additive manufacturing process, where the spinal implant or device, medical delivery device for a spinal implant or device, or further compositions (e.g., fillers) includes a sensor.

Within yet further embodiments of the invention, the spinal implant or device, medical delivery device for a spinal implant or device, or further compositions (e.g., fillers) provided herein can be sterilized suitable for use in a subject.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

B. Use of Spinal Implants to Deliver Therapeutic Agent(s)

As noted above, the present invention also provides drug-eluting spinal implants and drug-coated spinal implants which comprise one or more sensors, and which can be utilized to release a therapeutic agent (e.g., a drug) to a desired location within the body (e.g., a body tissue such as the intervertebral disc, the vertebral body, the spinal nerves or the spinal cord). Within related embodiments, a drug-eluting delivery device may be included within the spinal implant in order to release a desired drug upon demand (e.g., upon remote activation/demand, or based upon a timed schedule), or upon detection of an activating event (e.g., detection of an accelerometer of a significant impact event, or detection of loosening by a contact sensor) (see generally U.S. Patent App. No. 2011/0092948 entitled "Remotely Activated Piezoelectric Pump For Delivery of Biological Agents to the Intervertebral Disc and Spine", which is incorporated by reference in its entirety).

For example, within certain embodiments of the invention, biological agents can be administered along with or released from a spinal implant in order to increase bone growth, fibrosis or scarring within the implant (e.g., within or along with bone fragments in spinal cage, or along with naturally occurring or synthetic components which can be injected into the Nucleus Propulsis). Representative examples of suitable agents include, for example, irritants, silk, wool, talcum powder, metallic beryllium, and silica. Other agents which may be released by the spinal implant include components of extracellular matrix; fibronectin, polylysine, ethylenevinylacetate, and inflammatory cytokines such as TGFβ, PDGF, VEGF, bFGF, TNFα, NGF, GM-CSF, IGF-a, BMP and growth hormone, and adhesives such as cyanoacrylate (see U.S. Patent App. Nos. 2005/0149173 and 2005/0021126, both of which are incorporated by reference in their entirety).

Within other embodiments of the invention anti-scarring biological agents (e.g., drugs such as paclitaxel, sirolimus, or an analog or derivative of these), can be administered along with or released from a spinal implant in order to prevent scarring of the implant inappropriately, e.g., to prevent scaring or fibrosis in or around the spinal nerves or spinal cord (see, e.g., U.S. Pat. Nos. 7,491,188, U.S. Patent Application Nos. 2005/0152945, 2005/0187639, 2006/0079836, US 2009/0254063, US 2010/0023108, and US 2010/0042121).

Within other embodiments of the invention, anti-inflammatory agents, local anesthetics and pain-relief medications (e.g., drugs such as cortisone, dexamethasone, nonsteroidal anti-inflammatories, lidocaine, marcaine, morphine, codeine, narcotic pain relievers and analogs or derivatives of these) can be utilized to reduce post-operative pain and swelling and reduce the need for systemic pain relief therapy.

Within other embodiments a wide variety of additional therapeutic agents may be delivered (e.g., to prevent or treat an infection or to treat another disease state), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g, clindamycin); lipopeptides; macrolides (e.g., azithromycin); monobactams; nitrofurans; polypeptides (e.g, bacitracin); and tetracyclines.

Within preferred embodiments one or more sensors (e.g., pressure sensors, contact sensors, and/or position sensors) can be utilized to determine appropriate placement of the desired drug, as well as the quantity and release kinetics of drug (e.g. flow sensors, fluid volume sensors and accelerometers) to be released at a desired site.

C. Methods for Monitoring Infection

Within other embodiments spinal device/implants are provided comprising one or more temperature sensors. Such spinal devices/implants can be utilized to measure the temperature of the spinal device/implant, and in the local tissue adjacent to the spinal device/implant. Methods are also provided for monitoring changes in temperature over time, in order to determine and/or provide notice (e.g., to a patient and/or a healthcare provider) that an infection may be imminent. For example, temperature sensors may be included within one or more components of the spinal device/implant in order to allow early detection of infection that could allow preemptive treatment with antibiotics or surgical drainage and eliminate the need to surgically remove the spinal device/implant.

In certain embodiments of the present invention, metabolic and physical sensors can also be placed on or within the various components of a spinal device/implant in order to monitor for rare, but potentially life-threatening complications of spinal device/implants. In some patients, the spinal device/implant and surrounding tissues can become infected; typically from bacteria colonizing the patient's own skin that contaminate the surgical field or the device surface (often *Staphylococcus aureus* or *Staphylococcus epidermidis*). Sensors such as temperature sensors (detecting temperature increases), pH sensors (detecting pH decreases), and other metabolic sensors (e.g. oxygen content, $CO_2$ content, bacterial DNA detection assays) can be used to suggest the presence of infection on or around the spinal device/implant.

Hence, within one embodiment of the invention methods are provided for determining an infection associated with a spinal implant, comprising the steps of a) providing a spinal device and/or implant to a subject a monitored spinal device and/or implant as described herein, wherein the spinal implant and/or device comprises at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents")

D. Further Uses of Sensor-Containing Spinal Device/Implants in Healthcare

Sensors on spinal device/implants, and any associated medical devices have a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion (discussed later) and spinal device/implant performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, etc.), and to compare patient progress versus previous function and future expected function; also, since a significant amount of back pain can have a psychosocial origin, data such as this can help better distinguish somatic from psychosomatic symptoms. Better therapeutic decisions and better patient compliance can be expected when both the doctor and the patient have the benefit of observing the impact of various treatment modalities on patient rehabilitation, activity, function and overall performance.

E. Generation of Power

Within certain aspects of the invention, a small electrical generation unit can be positioned along an outer, or alternatively an inner, surface of the spinal device/implant, or associated medical device. Briefly, a variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body and movements within the body.

After the electricity is generated by one or more generators, the electricity can be transmitted to any one of the variety of sensors which is described herein. For example, it can be transmitted to any of the sensors shown in Figures. It may also be transmitted to the other sensors described herein. The transmission of the power can be carried out by any acceptable technique. For example, if the sensor is physically coupled to the spinal device/implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

F. Medical Imaging and Self-Diagnosis of Assemblies Comprising Spinal Device/Implants; Predictive Analysis and Predictive Maintenance Within other aspects of the invention methods are provided for imaging the spinal device/implant as provided herein, comprising the steps of (a) detecting the location of one or more sensors in the spinal device/implant, and/or associated medical device; and (b) visually displaying the location of said one or more sensors, such that an image of the spinal device/implant and/or medical device is created. Within various embodiments, the step of detecting may be done over time, and the visual display may thus show positional movement over time, such as during placement (intra-operatively) or during the post-operative (rehabilitative) period. Within certain preferred embodiments the image which is displayed is a three-dimensional image. Within preferred embodiments the various images may be collected and displayed in a time-sequence (e.g., as a 2D or 3D moving image or 'movie-like' image). Within other embodiment, the imaging techniques may be utilized post-operatively in order to examine the spinal device/implant, and/or to compare operation and/or movement of the device over time.

The present invention provides spinal device/implants and associated medical devices which are capable of imaging through the use of sensors over a wide variety of conditions. For example, within various aspects of the invention methods are provided for imaging the spinal device/implant (or portion thereof) or an assembly comprising the spinal device/implant, medical device or kit (as described herein) with sensors, comprising the steps of detecting the changes in sensors in, on, and or within the spinal device/implant, medical device or kit over time, and wherein the spinal device/implant, medical device or kit comprises sensors at a density of greater than 1, 2, 3, 4, 5, 6, 7, 8, 9, 10 or greater than 10 sensors per square centimeter.

Within other aspects the spinal device/implant medical device or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the spinal device/implant, medical device, or kit as described herein. As noted above, a wide variety of sensors can be utilized therein, including for example, contact sensors, strain gauge sensors, pressure sensors, fluid pressure sensors, position sensors, tissue chemistry sensors, tissue metabolic sensors, mechanical stress sensors, and temperature sensors.

For example, the spinal device/implant, medical device, or kit comprising sensors as described herein can be utilized to image anatomy through sensors which can detect positional movement. The sensors used can also include accelerometers and motion sensors to detect movement of the spinal device/implant due to a variety of physical changes. Changes in the position of the accelerometers and/or motion sensors over time can be used as a measurement of changes in the position of the spinal device/implant over time. Such positional changes can be used as a surrogate marker of spinal device/implant anatomy—i.e. they can form an "image" of the spinal device/implant to provide information on the size, shape, integrity, alignment and location of changes to the spinal device/implant, and/or spinal device/implant movement/migration. In particular, as noted above the image data can be collected over time, in order to visually show changes (e.g., a "movie" or "moving images", which may be in 2D or 3D).

Figure 20:
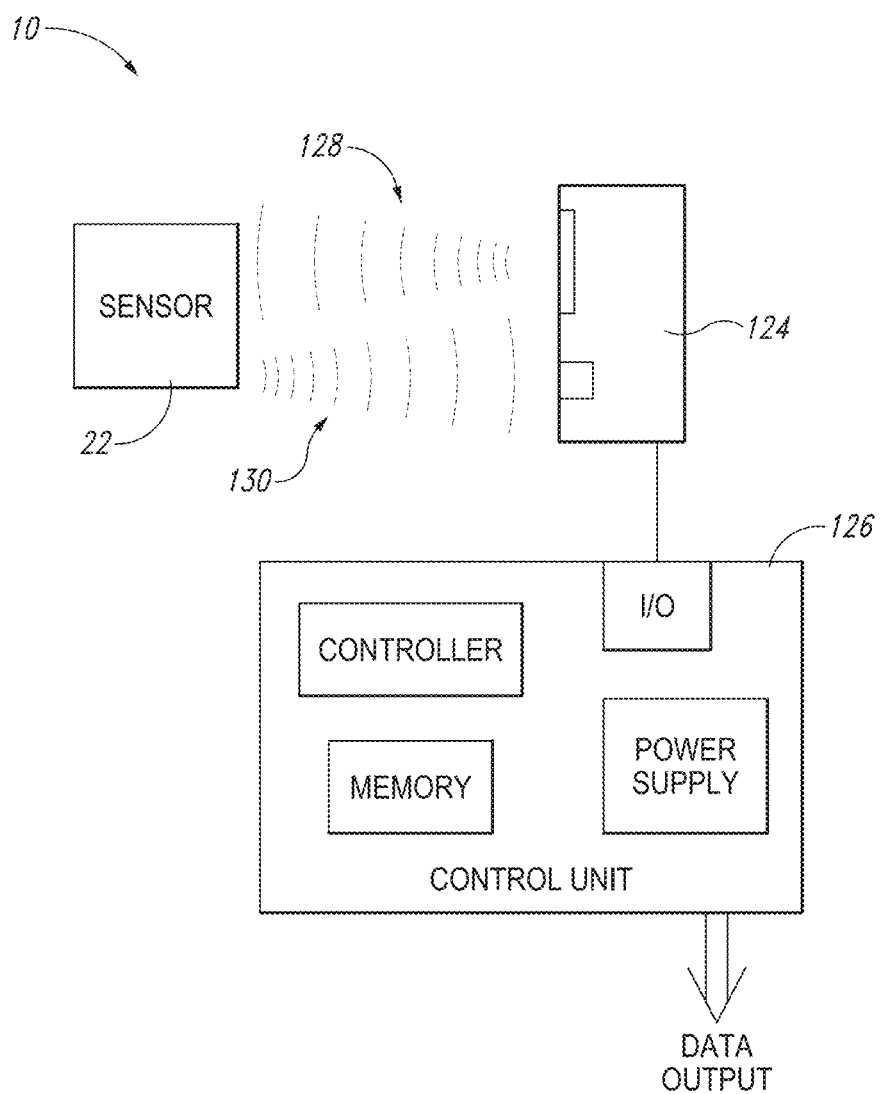
FIG. 20 illustrates an information and communication technology system embodiment arranged to process sensor data.

Certain exemplary embodiments will now be explained in more detail. One particular benefit is the live and in-situ monitoring of the patient's recovery with a spinal device/implant 10 having sensor 22 as shown in FIG. 20. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, instability, etc.)—and signals the device to obtain a reading at that time in order to allow the comparison of subjective/symptomatic data to objective/sensor data in an effort to better understand the underlying cause or triggers of the patient's symptoms.

In certain instances the spinal device/implant is of sufficient size and has more than sufficient space in order to house one or more processor circuits, CPUs, memory chips and other electrical circuits as well as antennas for sending and receiving the data. Within other embodiments, the associated medical device may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the spinal device/implant.

A patient with a spinal device/implant will generally have regular medical checkups. When the patient goes to the doctor's office for a medical checkup, the doctor will bring a reading device closely adjacent to the spinal device/implant 10, in this example the spinal device/implant, in order to transfer the data from the internal circuit inside the spinal device/implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the spinal device/implant to the doctor's computer or wireless device. The computer therefore analyzes the data for anomalies, unexpected changes over time, positive or negative trends, and other signs which may be indicative of the health of the patient and the operability of the spinal device/implant. For example, if the patient has decided to go skiing or jogging, the doctor will be able to monitor the effect of such activity on the spinal device/implant 10, including the accelerations and strains during the event itself. The doctor can then look at the health of the spinal device/implant in the hours and days after the event and compare it to data prior to the event to determine if any particular event caused long term damage, or if the activities subjected the spinal device/implant to forces beyond the manufacturer's performance specifications for that particular spinal device/implant. Data can be collected and compared with respect to the ongoing and long term performance of the spinal device/implant from the strain gauges, the contact sensors, the surface wear sensors, the accelerometer, the position sensors, or other sensors which may be present. Hence, within preferred embodiments the data can be collected over time, in order to visually show changes (e.g., a 2D or 3D "movie" or 'moving images").

In one alternative, the patient may also have such a reading device in their home which collates the data from the spinal device/implant on a periodic basis, such as once per day or once per week. As described above, the patient may also be able to "trigger" a device reading (via an external signaling/triggering device) as part of "event recording." For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different spinal device/implants can be compared in different patients (different sexes, weights, activity levels, etc.) to help manufacturers design better devices and assist surgeons and other healthcare providers in the selection of the right spinal device/implant for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

G. Methods of Monitoring Assemblies Comprising Spinal Device/Implants

Figure 21:
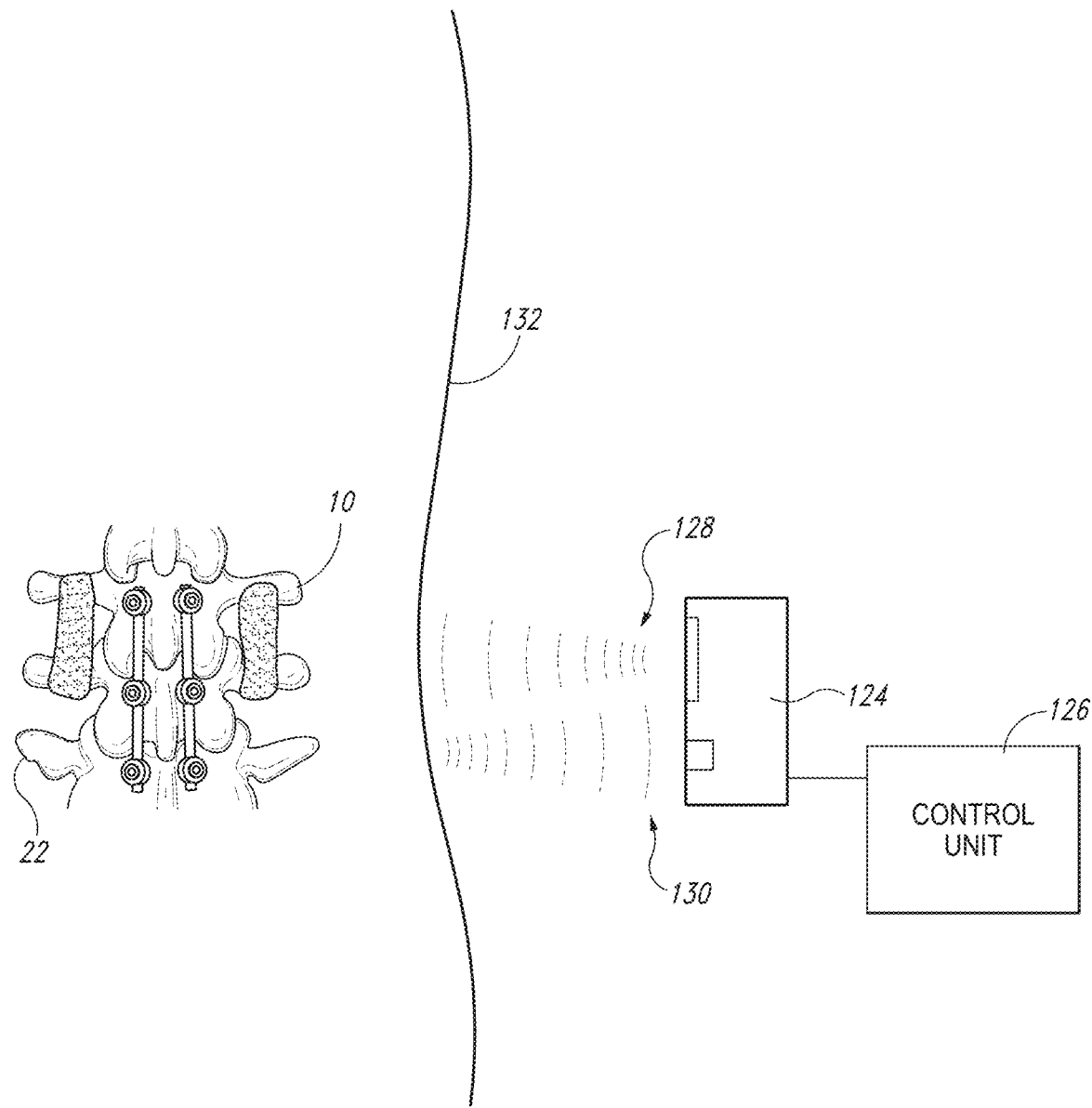
FIG. 21 is a block diagram of a sensor, interrogation module, and a control unit according to one embodiment of the invention.

As noted above, the present invention also provides methods for monitoring one or more of the spinal device/implants provided herein. For example, FIG. 21 illustrates a monitoring system usable with the spinal device/implant 10 as of the type shown in any one of the Figures described above. The monitoring system includes one or more sensors 22 an interrogation module 124, and a control unit 126. The sensor 22 can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 20, an interrogation module 124 outputs a signal 128. The signal 128 is a wireless signal, usually in the RF band, that contains power for the sensors 22 as well as an interrogation request that the sensors perform a sensing. Upon being interrogated with the signal 128, the sensors 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensors 22 and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the spinal device/implant. For example, the signal 128 may power up all sensors on the spinal device/implant at the same time and then send requests for data from each at different selected times so that with one interrogation signal 128 provided for a set time, such as 1-2 seconds, results in each of the sensors on the spinal device/implant collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

FIG. 21 illustrates the operation according to a one embodiment within a subject. The subject has an outer skin 132. As illustrated in FIG. 21, the interrogation module 124 and control unit 126 are positioned outside the skin 132 of the subject. The interrogation signal 128 passes through the skin of the subject with a wireless RF signal, and the data is received on a wireless RF signal 130 from the sensors within the spinal device/implant 10 back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

Figure 22:
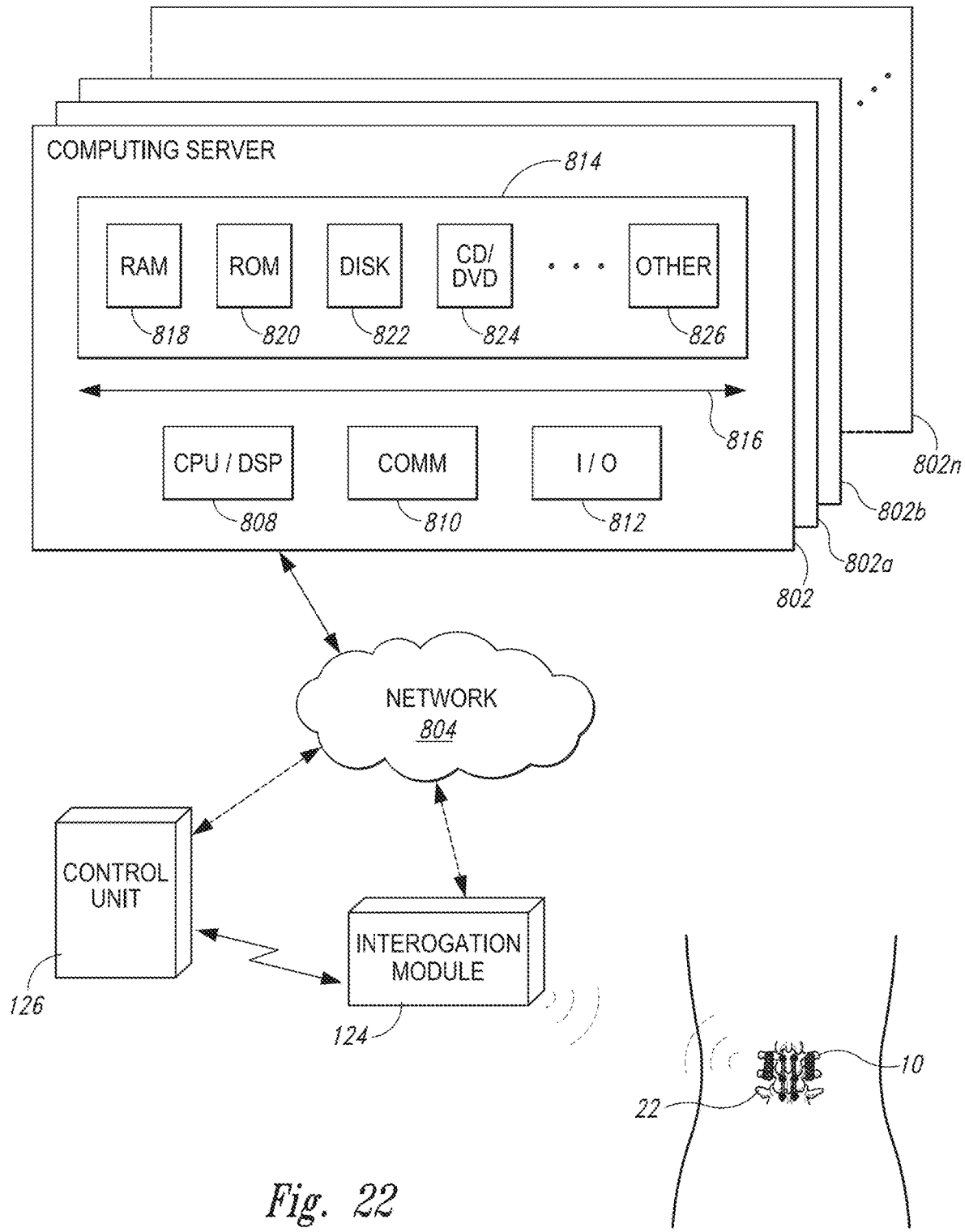
FIG. 22 is a schematic illustration of one or more sensors positioned on the spinal implant within a subject which is being probed for data and outputting data, according to one embodiment of the invention.

H. Collection, Transmission, Analysis, and Distribution of Data from Assemblies Comprising Spinal Device/Implants FIG. 22 illustrates one embodiment of an information and communication technology (ICT) system 800 arranged to process sensor data (e.g., data from the sensors 22). In FIG. 22, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 22 include computing servers 802, control units 126, interrogation units 124, and other devices that are not shown for simplicity.

In FIG. 22, one or more sensors 22 communicate with an interrogation module 124. The interrogation module 124 of FIG. 22 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 124 and the sensors 22, may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 22 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 22 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., spinal device/implant sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 22, sensor data from, e.g., sensors 22 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 22 includes one or more sensor data computer programs stored on a computer-readable medium. The computer program may optionally direct and/or receive data from one or more spinal device/implant sensors spinal device/implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of spinal device/implant sensor data is stored on a non-transitory computer-readable medium in storage module 814. The computer program is configured to identify a subject who has a wireless spinal device/implant inserted in his or her body. The wireless spinal device/implant may include one or more wireless sensors.

In some cases, the computer program identifies one subject, and in other cases, two or more subjects are identified. The subjects may each have one or more wireless spinal device/implants, and each wireless spinal device/implant may have one or more wireless sensors of the type described herein.

The computer program is arranged to direct the collection of sensor data from the wireless spinal device/implant devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 22:

```
Start
Open a secure socket layer (SSL)
Identify a subject
Communicate with a predetermined control unit
Request sensor data from the subject via the control unit
Receive sensor data
If the sensor data is encrypted
   THEN decrypt the sensor data
Store encrypted data in the selected storage locations
Aggregate the sensor data with other sensor data
Store encrypted data in the selected storage locations
Maintain a record of the storage transaction
Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, ambulance, truck, locomotive, tank, armored personnel carrier, etc.), (c) a building (e.g., a home, hospital, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, spinal device/implants utilizing a variety of sensors can be utilized to serve a variety of critical clinical functions, such as safe, accurate and less traumatic placement and deployment of the spinal device/implant, procedural and post-operative "real time" imaging of the spinal device/implant and the surrounding anatomy, the early identification of the development of spinal device/implant complications (often prior to becoming evident by other medical diagnostic procedures), and the patient's overall health status and response to treatment. Currently, post-operative (both in hospital and out-patient) evaluation of spinal device/implant patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes, radiation exposure). It can, therefore, be very difficult to accurately measure and follow the development or worsening of symptoms and evaluate "real life" spinal device/implant performance, particularly as they relate to patient activity levels, exercise tolerance, and the effectiveness of rehabilitation efforts and medications.

At present, neither the physician nor the patient has access to the type of "real time," continuous, objective, spinal device/implant performance measurements that they might otherwise like to have. Being able to monitor in situ spinal device/implant function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the spinal device/implant on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. Furthermore, their recovery experience can be shared via the web with other patients to compare their progress versus expected "norms" for function and rehabilitation and alert them to signs and symptoms that should be brought to their doctor's attention. From a public health perspective, the performance of different spinal device/implants can be compared in different patients (different sexes, disease severity, activity levels, concurrent diseases such as hypertension and diabetes, smoking status, obesity, etc.) to help manufacturers design better spinal device/implants and assist physicians in the selection of the right spinal device/implant for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (Latin, exempli gratia) is used herein to refer to a non-limiting example, and effectively means "for example".

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means ±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) An implantable medical device, comprising a pedicle screw, and a sensor.

2) An implantable medical device, comprising a spinal wire, and a sensor.

3) An implantable medical device, comprising a spinal rod, and a sensor.

4) An implantable medical device, comprising a spinal plate, and a sensor.

5) An implantable medical device, comprising a spinal cage, and a sensor.

6) An implantable medical device, comprising an artificial disc, and a sensor.

7) An implantable medical device kit, comprising a pedicle screw, a spinal rod and a sensor.

8) An implantable medical device kit, comprising a pedicle screw, a spinal plate and a sensor.

9) An implantable medical device, comprising a polymer and a sensor.

10) The medical device according to embodiment 9 wherein said polymer is selected from the group consisting of a polymethylmethacrylate, a methylmethacrylate—styrene copolymer, fibrin, polyethylene glycol, carboxymethylcellulose, and polyvinylalcohol.

11) An implantable medical device, comprising a kyphoplasty balloon, and a sensor.

12) The medical device according to any one of embodiments 1 to 11 wherein said sensor is located within said implant.

13) The medical device according to any one of embodiments 1 to 11 wherein said sensor is located on said implant.

14) The medical device according to any one of embodiments 1 to 13 wherein said device is sterile.

15) The medical device according to any one of embodiments 1 to 14 wherein said sensor is a contact sensor.

16) The medical device according to any one of embodiments 1 to 14 wherein said sensor is a pressure sensor.

17) The medical device according to any one of embodiments 1 to 14 wherein said sensor is an accelerometer sensor.

18) The medical device according to embodiment 17 wherein said accelerometer detects acceleration, tilt, vibration, shock and or rotation.

19) The medical device according to any one of embodiments 1 to 14 wherein said sensor is a temperature sensor.

20) The medical device according to any one of embodiments 1 to 14 wherein said sensor is a mechanical stress sensor.

21) The medical device according to any one of embodiments 1 to 14 wherein said sensor is selected from the group consisting of position sensors, chemical microsensors, and tissue metabolic sensors.

22) The medical device according to any one of embodiments 1 to 22 further comprising:
an electronic processor positioned upon and/or inside the spinal device/implant or medical device that is electrically coupled to sensors.

23) The medical device according to embodiment 22 wherein the electric coupling is a wireless coupling.

24) The medical device according to embodiment 22 further including:
a memory coupled to the electronic processor and positioned upon and/or inside the spinal device/implant or medical device.

25) The medical device according to any one of embodiments 1 to 24 wherein said sensor is a plurality of sensors which are positioned on or within said medical device at a density of greater than 1, 2, 3, 4, 5, 6, 7, 8, 9, 10 or 20 sensors per square centimeter.

26) The medical device according to any one of embodiments 1 to 24 wherein said sensor is a plurality of sensors which are positioned on or within said medical device at a density of greater than 1, 2, 3, 4, 5, 6, 7, 8, 9, 10 or 20 sensors per cubic centimeter.

27) A method comprising:
obtaining data from sensors positioned at a plurality of locations between on and/or within the medical device according to any one of embodiments 1 to 26 of a patient;
storing the data in a memory device located on or within the medical device; and
transferring the data from the memory to a location outside the medical device.

28) The method according to embodiment 27 further comprising the step of analyzing said data.

29) A method for detecting and/or recording an event in a subject with the medical device according to any one of embodiments 1 to 26, comprising the step of interrogating at a desired point in time the activity of one or more sensors within the medical device, and recording said activity.

30) The method according to embodiment 29 wherein the step of interrogating is performed by a subject which has said medical device.

31) The method according to embodiment 29 or 30 wherein said recording is performed on a wearable device.

32) The method according to any one of embodiments 29, 30 or 31, wherein said recording, or a portion thereof, is provided to a health care provider.

33) A method for imaging the medical device in the spine, comprising the steps of
(a) detecting the location of one or more sensors in the medical device according to any one of embodiments 1 to 26; and
(b) visually displaying the location of said one or more sensors, such that an image of the medical device, or a portion thereof, in the spine is created.

34) The method according to embodiment 33 wherein the step of detecting occurs over time.

35) The method according to embodiment 33 or 34, wherein said visual display shows changes in the positions of said sensors over time, and/or changes in temperature of the sensors or surrounding tissue over time.

36) The method according to any one of embodiments 33 to 35 wherein said visual display is a three-dimensional image of said medical device in the spine.

37) A method for inserting the spinal device/implant according to any one of embodiments 1 to 26, comprising the steps of
(a) inserting an implantable medical device according to any one of embodiments 1 to 26 into a subject; and
(b) imaging the placement of said medical device according to the method of an one of embodiments 33 to 36.

38) A method for examining the spinal device/implant according to any one of embodiments 1 to 26 which has been previously inserted into a patient, comprising the step of imaging the spinal device/implant according to the method of any one of embodiments 33 to 36.

39) A method of monitoring a spinal device/implant within a subject, comprising:

transmitting a wireless electrical signal from a location outside the body to a location inside the subject's body;

receiving the signal at a sensor positioned on a spinal device/implant according to any one of embodiments 1 to 26 located inside the body;

powering the sensor using the received signal;

sensing data at the sensor; and outputting the sensed data from the sensor to a receiving unit located outside of the body.

40) The method according to embodiment 39 wherein said receiving unit is a watch, wrist band, cell phone or glasses.

41) The method according to embodiments 39 or 40 wherein said receiving unit is located within a subject's residence or office.

42) The method according to embodiments any one of embodiments 39 to 41 wherein said sensed data is provided to a health care provider.

43) The method according to any one of embodiments 39 to 42 wherein said sensed data is posted to one or more websites.

44) A non-transitory computer-readable storage medium whose stored contents configure a computing system to perform a method, the method comprising:

identifying a subject, the identified subject having at least one wireless spinal device/implant according to any one of embodiments 1 to 26, each wireless spinal device/implant having one or more wireless sensors;

directing a wireless interrogation unit to collect sensor data from at least one of the respective one or more wireless sensors; and receiving the collected sensor data.

45) The non-transitory computer-readable storage medium of embodiment 44 whose stored contents configure a computing system to perform a method, the method further comprising:

identifying a plurality of subjects, each identified subject having at least one wireless spinal device/implant, each wireless spinal device/implant having one or more wireless sensors;

directing a wireless interrogation unit associated with each identified subject to collect sensor data from at least one of the respective one or more wireless sensors;

receiving the collected sensor data; and aggregating the collected sensor data.

46) The non-transitory computer-readable storage medium of embodiment 44 whose stored contents configure a computing system to perform a method, the method further comprising:

removing sensitive subject data from the collected sensor data; and parsing the aggregated data according to a type of sensor.

47) The non-transitory computer-readable storage medium of embodiment 44 whose stored contents configure a computing system to perform a method, wherein directing the wireless interrogation unit includes directing a control unit associated with the wireless interrogation unit.

48) The non-transitory computer readable storage medium according to any one of embodiments 44 to 47, wherein said spinal device/implant is according to any one of embodiments 1 to 26.

49) The storage medium according to any one of embodiments 44 to 48 wherein said collected sensor data is received on a watch, wrist band, cell phone or glasses.

50) The storage medium according to any one of embodiments 44 to 49 wherein said collected sensor data is received within a subject's residence or office.

51) The storage medium according to any one of embodiments 44 to 50 wherein said collected sensed data is provided to a health care provider.

52) The storage medium according to any one of embodiments 44 to 51 wherein said sensed data is posted to one or more websites.

53) The method according to any one of embodiments 39 to 43, or storage medium according to any one of embodiments 44 to 52, wherein said data is analyzed.

54) The method or storage medium according to embodiment 53 wherein said data is plotted to enable visualization of change over time.

55) The method or storage medium according to embodiments 53 or 54 wherein said data is plotted to provide a three-dimensional image.

56) A method for determining degradation of a spinal device/implant, comprising the steps of a) providing to a subject a spinal device/implant according to any one of embodiments 1 to 26, and b) detecting a change in a sensor, and thus determining degradation of the spinal device/implant.

57) The method according to embodiment 55 wherein said sensor is capable of detecting one or more physiological and/or locational parameters.

58) The method according to embodiments 55 or 56 wherein said sensor detects a location within the subject.

59) The method according to any one of embodiments 55 to 58 wherein said sensor moves from its original location, thereby indicating degradation of the spinal device/implant.

60) The method according to any one of embodiments 55 to 59 wherein the step of detecting is a series of detections over time.

61) A method for determining an infection associated with a spinal device/implant, comprising the steps of a) providing to a subject a spinal device/implant according to any one of embodiments 1 to 26, wherein said spinal device/implant comprises at least one temperature sensor and/or metabolic sensor, and b) detecting a change in said temperature sensor and/or metabolic sensor, and thus determining the presence of an infection.

62) The method according to embodiment 60 wherein the step of detecting is a series of detections over time.

63) The method according to embodiments 60 or 61 wherein said change is greater than a 1% change over the period of one hour.

64) The method according to any one of embodiments 60 to 62 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An implantable medical device comprising:
   a first spinal cage having a first flattened vertical side and at least one first sensor associated with the first flattened vertical side; and
   a second spinal cage having a second flattened vertical side and at least one second sensor associated with the second flattened vertical side,
   wherein the first flattened vertical side and the second flattened vertical side are configured to allow side-by-side placement of the first spinal cage and the second spinal cage in an intervertebral space of a spine, with the at least one first sensor and the at least one second sensor placed in a matched arrangement relative to each other to detect movement between the first spinal cage and the second spinal cage.

2. The implantable medical device of claim 1, wherein at least one of the first spinal cage and the second spinal cage is hollow to allow the incorporation of bone graft material.

3. The implantable medical device of claim 1, wherein at least one of the first spinal cage and the second spinal cage is hollow and cylindrical devices composed of titanium, titanium alloys, stainless steel, or polymers.

4. The implantable medical device of claim 1, wherein at least one of the first spinal cage and the second spinal cage is composed of titanium, titanium alloy, stainless steel, or polymer.

5. The implantable medical device of claim 1, wherein the at least one first sensor and the at least one second sensor placed in a matched arrangement are contact sensors.

6. The implantable medical device of claim 5, wherein one or both of the first spinal cage and the second spinal cage include at least one of a strain gauge sensor, a pressure sensor, a fluid pressure sensor, a position sensor, a shock sensor, a rotation sensor, a vibration sensor, a tilt sensor, a tissue chemistry sensor, a tissue metabolic sensor, a mechanical stress sensor, and a temperature sensor.

7. The implantable medical device of claim 1, wherein the at least one first sensor and the at least one second sensor placed in a matched arrangement are accelerometers.

8. The implantable medical device of claim 7, wherein one or both of the first spinal cage and the second spinal cage include at least one of a strain gauge sensor, a pressure sensor, a fluid pressure sensor, a position sensor, a shock sensor, a rotation sensor, a vibration sensor, a tilt sensor, a tissue chemistry sensor, a tissue metabolic sensor, a mechanical stress sensor, and a temperature sensor.

9. The implantable medical device of claim 1, wherein the at least one first sensor includes a first contact sensor and a first accelerometer, and the at least one second sensor comprises a second contact sensor placed in a matched arrangement with the first contact sensor and a second accelerometer placed in a matched arrangement with the first accelerometer.

10. The implantable medical device of claim 9, wherein one or both of the first spinal cage and the second spinal cage include at least one of a strain gauge sensor, a pressure sensor, a fluid pressure sensor, a position sensor, a shock sensor, a rotation sensor, a vibration sensor, a tilt sensor, a tissue chemistry sensor, a tissue metabolic sensor, a mechanical stress sensor, and a temperature sensor.

11. The implantable medical device of claim 1, wherein the at least one of the first sensor is placed on the first flattened vertical side of the first spinal cage and the at least one second sensor is placed on the second flattened vertical side of the second spinal cage.

12. The implantable medical device of claim 11, wherein the first flattened vertical side of the first spinal cage comprises a perforated wall, and the second flattened vertical side of the second spinal cage comprises a perforated wall.

13. The implantable medical device of claim 1, further comprising:
    a first electronic processor coupled to the at least one first sensor and to a first memory chip, and programmed to collect first data from the at least one first sensor based on a schedule; and
    a second electronic processor coupled to the at least one second sensor and to a second memory chip and programmed to collect second data from the at least one second sensor based on a schedule, where the first data and the second data enable a detection of movement between the first spinal cage and the second spinal cage.

14. The implantable medical device of claim 13, wherein the first electronic processor and the first memory chip are inside the first spinal cage, and the second electronic processor and the second memory chip are inside the second spinal cage.

* * * * *